(12) United States Patent
Gruber et al.

(10) Patent No.: US 7,763,033 B2
(45) Date of Patent: Jul. 27, 2010

(54) SYSTEM AND METHODS FOR PREVENTING INTRAVASATION DURING INTRAUTERINE PROCEDURES

(75) Inventors: William H. Gruber, Southborough, MA (US); Ronald D. Adams, Holliston, MA (US); Kevin G. Connors, Wellesley, MA (US); Geoffrey B. Pardo, Cambridge, MA (US); James Daniel Cole, Wayland, MA (US); J. Christopher Flaherty, Topsfield, MA (US)

(73) Assignee: Interlace Medical, Inc., Framingham, MA (US)

( * ) Notice: Subject to any disclaimer, the term of this patent is extended or adjusted under 35 U.S.C. 154(b) by 186 days.

(21) Appl. No.: 11/852,116

(22) Filed: Sep. 7, 2007

(65) Prior Publication Data
US 2008/0097467 A1    Apr. 24, 2008

Related U.S. Application Data

(60) Provisional application No. 60/852,842, filed on Oct. 18, 2006.

(51) Int. Cl.
*A61B 17/42* (2006.01)
*A61M 29/00* (2006.01)

(52) U.S. Cl. .................................. 606/119; 606/193
(58) Field of Classification Search ............ 606/119, 606/193
See application file for complete search history.

(56) References Cited

U.S. PATENT DOCUMENTS

| | | |
|---|---|---|
| 2,849,002 A | 8/1958 | Oddo, et al. |
| 4,198,981 A | 4/1980 | Sinnreich |
| 5,108,414 A | 4/1992 | Enderle et al. |
| 5,222,971 A | 6/1993 | Willard et al. |
| 5,361,752 A | 11/1994 | Moll et al. |
| 5,377,668 A | 1/1995 | Ehmsen et al. |
| 5,402,772 A | 4/1995 | Moll et al. |
| 5,450,843 A | 9/1995 | Moll et al. |
| 5,522,790 A | 6/1996 | Moll et al. |
| 5,738,629 A | 4/1998 | Moll et al. |
| 5,743,850 A | 4/1998 | Moll et al. |

(Continued)

FOREIGN PATENT DOCUMENTS

EP    0044877    2/1982

(Continued)

OTHER PUBLICATIONS

International Search Report and Written Opinion Received in PCT/US07/83982 Dated May 20, 2008.

(Continued)

*Primary Examiner*—Todd E. Manahan
*Assistant Examiner*—Kevin Everage
(74) *Attorney, Agent, or Firm*—Knobbe Martens Olson & Bear LLP

(57) ABSTRACT

Systems, methods, apparatus and devices for performing improved gynecologic and urologic procedures are disclosed. Patient benefit is achieved through improved outcomes, reduced pain, especially peri-procedural pain, and reduced recovery times. The various embodiments enable procedures to be performed outside the hospital setting, such as in a doctor's office or clinic. Distension is achieved mechanically, rather than with liquid distension media, thereby eliminating the risk of intravasation.

20 Claims, 17 Drawing Sheets

U.S. PATENT DOCUMENTS

| | | | |
|---|---|---|---|
| 5,743,851 | A | 4/1998 | Moll et al. |
| 5,749,889 | A | 5/1998 | Bacich et al. |
| 5,823,945 | A | 10/1998 | Moll et al. |
| 5,855,549 | A | 1/1999 | Newman |
| 5,865,728 | A | 2/1999 | Moll et al. |
| 5,899,915 | A | 5/1999 | Saadat |
| 5,961,444 | A | 10/1999 | Thompson |
| 6,032,673 | A | 3/2000 | Savage et al. |
| 6,039,748 | A | 3/2000 | Savage et al. |
| 6,190,357 | B1 | 2/2001 | Ferrarl et al. |
| 6,319,272 | B1 | 11/2001 | Brenneman et al. |
| 6,432,116 | B1 | 8/2002 | Callister et al. |
| 6,471,644 | B1 | 10/2002 | Sidor, Jr. |
| 6,494,909 | B2 | 12/2002 | Greenhalgh |
| 6,605,037 | B1 | 8/2003 | Moll et al. |
| 6,673,101 | B1 | 1/2004 | Fitzgerald et al. |
| 6,709,667 | B1 | 3/2004 | Lowe et al. |
| 6,763,833 | B1 | 7/2004 | Khera et al. |
| 6,827,703 | B1 | 12/2004 | Ackerman |
| 6,896,682 | B1 | 5/2005 | Mcclellan et al. |
| 6,979,332 | B2 | 12/2005 | Adams |
| 6,997,925 | B2 | 2/2006 | Maguire et al. |
| 2002/0010457 | A1* | 1/2002 | Duchon et al. ............ 604/515 |
| 2004/0049211 | A1 | 3/2004 | Tremulis et al. |
| 2005/0267408 | A1 | 12/2005 | Grandt et al. |
| 2005/0277975 | A1 | 12/2005 | Saadat et al. |
| 2006/0004436 | A1 | 1/2006 | Amarant et al. |
| 2006/0064074 | A1 | 3/2006 | Mallaby |
| 2007/0225744 | A1 | 9/2007 | Nobles et al. |
| 2008/0051758 | A1* | 2/2008 | Rioux et al. ............ 604/509 |
| 2008/0245371 | A1 | 10/2008 | Gruber et al. |
| 2008/0249366 | A1 | 10/2008 | Gruber et al. |
| 2008/0249553 | A1 | 10/2008 | Gruber et al. |

FOREIGN PATENT DOCUMENTS

| | | |
|---|---|---|
| EP | 0141589 | 5/1985 |
| EP | 782427 | 2/1996 |
| EP | 0812573 | 12/1997 |
| EP | 1635695 | 1/2005 |
| FR | 2701401 | 8/1994 |

OTHER PUBLICATIONS

International Search Report and Written Opinion Received in PCT/US08/59493 Dated Apr. 4, 2008.
International Search Report and Written Opinion Received in PCT/US07/83833 Dated Jun. 5, 2008.
International Search Report and Written Opinion Received in PCT/US08/59504 Dated Sep. 4, 2008.
International Search Report and Written Opinion Received in PCT/US08/59503 Dated Sep. 5, 2008.
U.S. Appl. No. 11/852,151, including its prosecution history, and the Office Actions, Gruber, et al.
U.S. Appl. No. 11/936,003, including its prosecution history, and the Office Actions, Gruber, et al.
U.S. Appl. No. 11/951,853, including its prosecution history, and the Office Actions, Gruber, et al.
U.S. Appl. No. 11/852,142, including its prosecution history, and the Office Actions, Gruber, et al.
U.S. Appl. No. 11/852,121, including its prosecution history, and the Office Actions, Adams, et al.
U.S. Appl. No. 11/852,200, including its prosecution history, and the Office Actions, Adams, et al.
U.S. Appl. No. 11/923,357, including its prosecution history, and the Office Actions, Gruber, et al.
U.S. Appl. No. 11/923,482, including its prosecution history, and the Office Actions, Gruber, et al.
International Search Report and Written Opinion Received in PCT/US07/79449 Dated Jan. 28, 2008.
U.S. Appl. No. 12/432,691, including its prosecution history, and the Office Actions, Adams, et al.
U.S. Appl. No. 12/432,702, including its prosecution history, and the Office Actions, Chin, et al.
U.S. Appl. No. 12/432,686, including its prosecution history, and the Office Actions, Sullivan, et al.
U.S. Appl. No. 12/432,675, including its prosecution history, and the Office Actions, Churchill, et al.
U.S. Appl. No. 12/432,647, including its prosecution history, and the Office Actions, Litscher, et al.

* cited by examiner

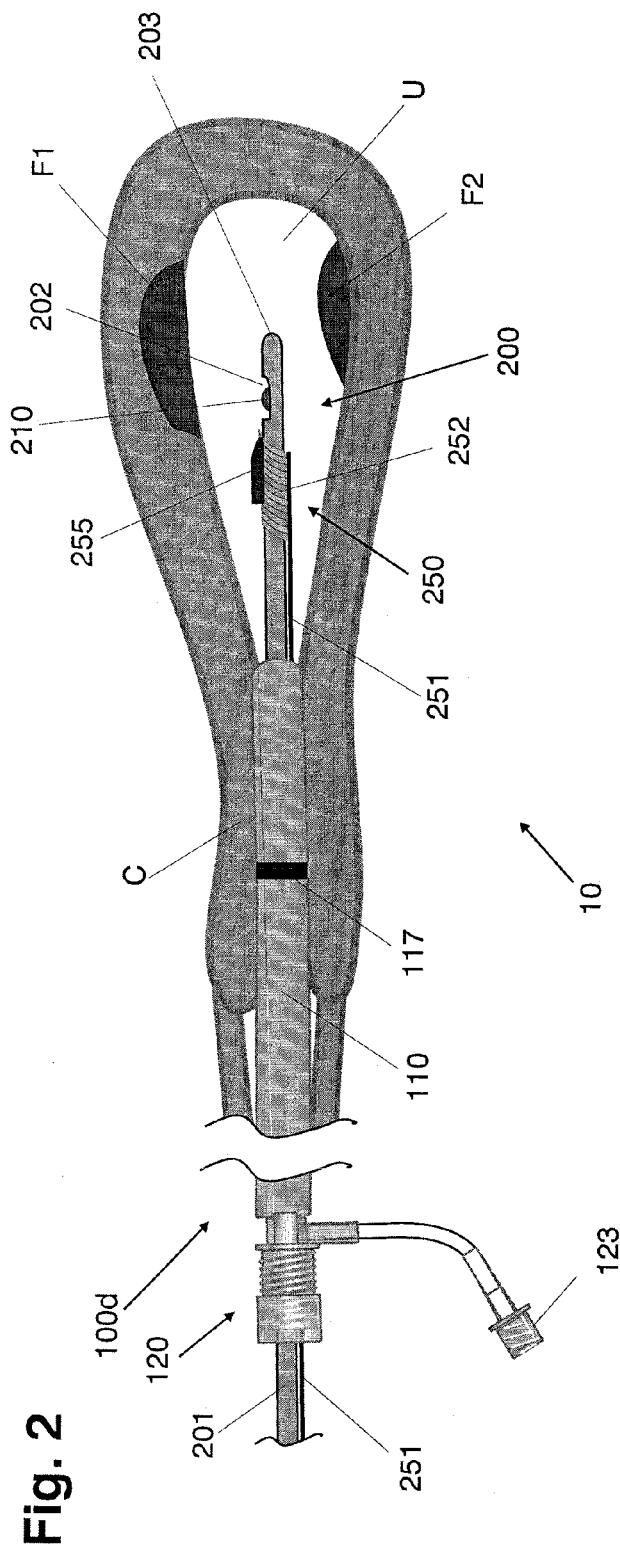
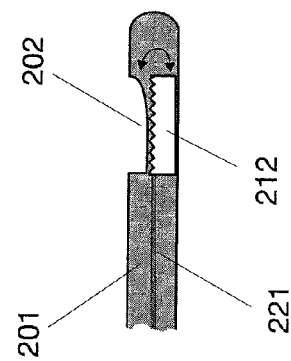
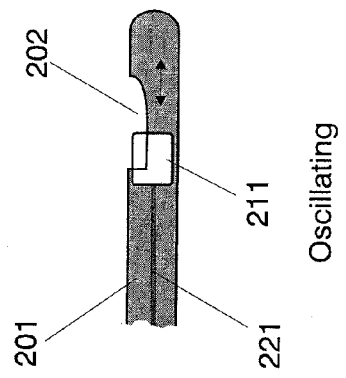
Fig. 2
Fig. 2A Oscillating
Fig. 2B
Fig. 2C

SYSTEM AND METHODS FOR PREVENTING INTRAVASATION DURING INTRAUTERINE PROCEDURES

PRIORITY INFORMATION

This application claims priority under 35 U.S.C. §119 to U.S. Provisional Patent Application Ser. No. 60/852,842, filed Oct. 18, 2006, the disclosure of which is incorporated in its entirety herein by reference.

BACKGROUND OF THE INVENTION

1. Field of the Invention

The present invention relates to systems, methods, apparatus and devices for performing one or more gynecologic and urologic procedures. More particularly, devices and combinations of devices provide simplified use and enhanced safety to support performance of various diagnostic and therapeutic procedures in the doctor's office setting.

2. Description of the Related Art

Currently available gynecologic products are difficult to use and often have limited use and functionality. Treatment of gynecologic disorders and ailments is most often performed in a hospital and bears a large cost due to the setting and the support personnel required. Treatment options and modalities are also limited, such that the patient may not be offered the best option for her particular condition.

There is therefore a need for improved gynecologic systems, methods and devices that simplify use, offer improved functionality and enhanced safety.

SUMMARY OF THE INVENTION

There is provided in accordance with one aspect of the present invention, a method of preventing intravasation during an intrauterine procedure. The method comprises the steps of transcervically accessing the uterus with an elongate tubular sheath. A mechanical distension device is introduced through the sheath and into the uterus. The mechanical distension device is used to distend the uterus and expose a site. A therapeutic or diagnostic procedure may be performed at the site.

The transcervically accessing step may comprise advancing the sheath over a guidewire. The transcervically accessing step may be accomplished under local anesthesia.

The mechanical distension step achieves an equivalent distension to that achieved by introduction of a liquid distension media at a pressure of at least about 40 mm Hg. In some embodiments, the mechanical distension step is utilized to achieve an equivalent distension to that achieved by introduction of a liquid distension media at a pressure of at least about 70 mm Hg.

The method may additionally comprise the step of dilating the cervix prior to the transcervically accessing step. The performing a procedure step may comprise treating a uterine fibroid.

In accordance with another aspect of the present invention, there is provided a method of performing a procedure in the uterus. The method comprises the steps of transcervically accessing the uterus with an elongate flexible tubular sheath, having a proximal end, a distal end and at least one lumen extending therethrough. The sheath has an outside diameter of no more than about 9 mm.

The uterus is distended to expose a site, and a visualization device is introduced through the sheath to visualize the site. A procedure is performed at the site. The procedure may be a diagnostic procedure or a therapeutic procedure.

In some embodiments, the outside diameter of the sheath is less than about 8 mm, generally less than about 7 mm, and preferably less than about 6 mm.

Further features and advantages of the present invention will become apparent from the detailed description of preferred embodiments which follows, when considered together with the attached drawings and claims.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIG. 2 illustrates a side sectional view of an exemplary embodiment of a system of the present invention, wherein an introducer includes a radiopaque ring and is shown deployed in the cervix, and a tissue removal device with a side-saddle camera has been advanced through the introducer and into the uterus of a patient;

FIG. 2A illustrates a side sectional view of the distal end of a tissue removal device consistent with the present invention, wherein the device includes an oscillating cutter;

FIG. 2B illustrates a side sectional view of the distal end of another tissue removal device consistent with the present invention, wherein the device includes a rotating cutter;

FIG. 2C illustrates a side sectional view of the distal end of a tissue removal device and side-saddle camera, consistent with the present invention;

DETAILED DESCRIPTION OF THE PREFERRED EMBODIMENT

Figure 1:
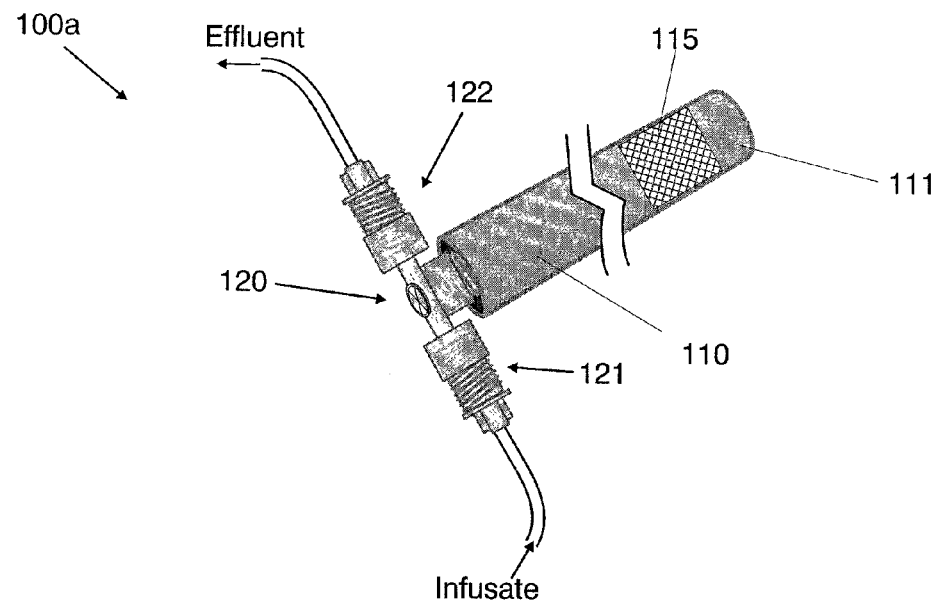
FIG. 1 illustrates a perspective view of an exemplary embodiment of an introducer consistent with the present invention.

To facilitate an understanding of the invention, a number of terms are defined immediately herebelow.

As used herein, the term "trans-vaginal-wall" refers to devices or procedures which enter the vaginal opening, travel down the vaginal canal, and exit through the vaginal wall proximal to the cervix.

As used herein, the term "trans-cervical" refers to devices or procedures which enter the vaginal opening, travel down the vaginal canal, pass through the cervical canal and enter the uterus.

As used herein, the term "trans-uteral" refers to devices or procedures which pass through the wall of the uterus.

As used herein, the term "drug" refers to all drugs and other agents that may be included in the systems, methods apparatus and devices of the present invention; either by including the drug into a coating or an integral reservoir of a component; or by provided to the patient through other means such as via a lumen and exit port which is in fluid communication with a supply of the drug such as an infusion pump or syringe. Drugs shall include not only pharmaceutical compounds such as anesthetics, anti-thrombotics, thrombotics, anti-bacterial drugs and chemotherapeutics, but also other agents such as ionic solutions, hormones, genes, vitamins, clotting agents, naturally occurring substances such as extracts from plants, and any other compound or agent applicable to the procedures contained herein.

As used herein, "patient" refers to any animal, such as a mammal and preferably a human. Specific examples of "patients" include but are not limited to: individuals requiring medical assistance and healthy individuals.

Systems, methods, apparatus and devices consistent with the invention provide improved diagnostic and therapeutic gynecologic and urologic procedures and outcomes. The simplified, safer use provided allows these procedures to be performed in locations such as a doctor's office or health clinic, eliminating the high costs associated with a hospital setting. Specific devices of the present invention reduce the pain encountered by the patient during and after the associated diagnostic or therapeutic procedure. The devices and apparatus provide to the clinician operator precision in both manipulation and device actions, and often allow reversibility of one or more steps of the procedure without undesirable consequence. Inadvertent tissue trauma is avoided with blunting of tips and other tissue-contacting surfaces. Simplified mechanisms, miniaturized geometries and improved methods reduce procedure times and trauma, and also the associated infection risk and blood loss. Intravasation, the entry of foreign matter in a blood vessel, is also reduced.

An introducer is provided which can be placed into the patient to provide a stabile, working platform to support simplified introduction of one or more diagnostic, treatment or other devices. The introducer includes an elongate shaft with one or two or more internal lumens. The proximal end of the shaft may include one or more access ports, such as fluid access ports and device entry ports, as well as one or more controls such as buttons, knobs or levers used to manipulate the introducer or activate a mechanical or electronic module of the introducer. The introducer preferably accepts devices comprising elongate shafts, sequentially or simultaneously. The introducer system also permits the administration and or removals of fluid from the patient, such as fluid administered to the uterus, while also providing fluid stasis or maintaining stasis to a maximum pressure at which fluid can be automatically evacuated. The introducer system also permits the administration of one or more drugs, such as anesthetic drugs or clotting agents. The introducer system may be introduced through the cervix and into the uterus, through the vaginal wall to a location outside the uterus (trans-vaginal-wall), or through another entry path to a specific anatomical location within the patient.

Systems are provided that enable and/or perform diagnostic, therapeutic or combined diagnostic and therapeutic gynecologic and urologic procedures. The systems preferably include one or more of the introducer, a treatment device, a tissue removal device, a subsonic treatment device, a drug delivery device, a dilating device, a vaginal-wall-crossing device, a scaffolding device, a volume occupying device, a stabilizing device, a visualization apparatus and a navigation apparatus, all of the present invention, and other devices applicable to gynecological procedures. The systems of the present invention are simple to use, and provide reduced risks while enhancing outcomes.

Treatment Devices are provided which allow a clinician to perform, individually or in combination with additional devices, one or more gynecologic and urologic procedures. The treatment devices provided include but are not limited to: devices which remove, denature or otherwise treat undesired tissue; devices which modify the structure of a vessel such as a fallopian tube or blood vessel occlusion device; drug delivery devices; and other therapeutic or diagnostic devices. The treatment devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. The treatment devices of the present invention may additionally or alternatively perform a diagnostic function. These treatment devices may provide multiple functions, such as diagnostic or treatment functions including applying a tamponade force to bleeding tissue or distending tissue such as uteral wall tissue.

Treatment devices include tissue removal devices which can be inserted through the introducer of the present invention and be subsequently operated to remove tissue. Tissue removal device are often arranged with vacuum assemblies which provide a vacuum proximate a tissue removal element and evacuate the tissue to be removed to a site outside of the patient's body.

Treatment devices include subsonic treatment devices which also can be inserted through the introducer of the present invention and subsequently deliver subsonic energy to disrupt or otherwise modify tissue such as a fibroid.

Treatment devices include drug delivery devices which can be placed into the patient and controllably deliver a drug to a specific area of tissue or space, such as the vaginal wall, cervix, uterus, uteral wall or fallopian tube as well as a specific fibroid, polyp, tumor or other tissue mass. These drug delivery devices may provide additional functions, such as diagnostic or treatment functions including applying a tamponade force to bleeding tissue or distending tissue such as uteral wall tissue.

Dilating devices are provided which can be used to dilate the cervix, a penetration tract in the vaginal wall, or other tissue. The dilating devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. Specific embodiments include "smart" dilation systems and methods which measure one or more parameters (e.g. device parameters such as strain or pressure or patient parameters such as EKG, EEG, blood pressure or respiration). One or more algorithms are applied to the measured parameters and used to control one or more dilation parameters such as rate, force and magnitude. These dilation devices may be integrated into another device, such as an introducer, a treatment device, or other device of the present invention. These dilation devices may provide additional or alternative functions, such as diagnostic or treatment functions including applying a tamponade force to bleeding tissue, distending tissue such as uteral wall tissue, or delivering a drug to tissue. The dilating devices of the present invention are typically configured to dilate to a diameter less than 9 mm, preferably between 5 and 8 mm, and more preferably between 2 and 5 mm. The dilating devices of the present invention are typically dilated to a pressure not to exceed 300 psi (e.g. balloon dilation pressure), and preferably less than 150 psi.

Vaginal-wall-crossing devices are provided that permit safe introduction of one or more devices, such as the introducer of the present invention, from inside the vaginal canal, through the vaginal wall to various anatomical locations including but not limited to: the outer wall of the uterus; the outer wall of the fallopian tubes; the ovaries; intra-abdominal locations; other locations and combinations thereof. The crossing devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. In a preferred embodiment, a guidewire is first placed through the vaginal wall, and one or more devices are placed over-the-wire. These crossing devices may provide additional or alternative functions, such as diagnostic or treatment functions including delivering a drug to tissue.

Distension devices are provided which can be introduced into a space, such as the uterus, and apply a force to tissue. The distension devices include without limitation, for example, scaffolding devices or the like. The distension devices are preferably inserted through the introducer of the present invention. The distension devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. These distension devices may provide additional or alternative functions, such as diagnostic or treatment functions including applying a tamponade force to bleeding tissue or delivering a drug to tissue. These distension devices are preferably inserted into the uterus of a patient such that the scaffolding assembly preferably distends the uteral cavity to a volume equivalent to that which would be attained via a liquid distension media at a pressure of at least 40 mm of HG but not greater than 100 mm HG and preferably approximating 70 mm Hg.

Volume Occupying devices are provided which can be introduced into a space, such as the uterus, and occupy space within the uterus. The volume occupying devices are preferably inserted through the introducer of the present invention. The volume occupying devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. These volume occupying devices provide the function of taking up space in a cavity, such as taking up space in the uterus to reduce the amount of fluid delivered to the uterus in a diagnostic or therapeutic procedure. These volume occupying devices may provide additional or alternative functions, such as diagnostic or treatment functions including applying a tamponade force to bleeding tissue, distending tissue such as uteral wall tissue, or delivering a drug to tissue.

Stabilizing devices are provided which are used to stabilize one or more separate devices, such as a treatment device of the present invention. Stabilizing devices may include magnets which attract a corresponding magnet integral to the separate device such as to position a treatment device proximate to tissue to be treated. The stabilizing devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device such as an electromagnet located in the distal portion of the shaft. These stabilizing devices may provide additional or alternative functions, such as diagnostic or treatment functions including applying a tamponade force to bleeding tissue, distending tissue such as uteral wall tissue, or delivering a drug to tissue.

Visualization apparatus are provided which provide enhanced imaging of target anatomical locations within the patient. The apparatus include one or more of: miniaturized cameras; infrared cameras; deployable light sources; stabilizing mechanisms; image stabilizing modules and processing; and improved and cost-reduced displays (e.g. a laptop screen display). The visualization apparatus preferably include one or more devices comprising an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. These visualization apparatus may provide additional or alternative functions, such as diagnostic or treatment functions including applying a tamponade force to bleeding tissue, distending tissue such as uteral wall tissue, or delivering a drug to tissue.

Navigating apparatus are provided which enable a clinician to navigate one or more diagnostic or therapeutic devices to perform a gynecologic procedure. The navigation apparatus preferably include one or more of: an electromagnetic (EM) beacon and/or receiver; a light emitter and/or detector; and a magnetic source and/or a detector. The navigation apparatus preferably include one or more devices comprising an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. These navigation apparatus may provide additional or alternative functions, such as diagnostic or treatment functions including applying a tamponade force to bleeding tissue, distending tissue such as uteral wall tissue, or delivering a drug to tissue.

Shape-modifying wires are provided which are slidingly received by one or more lumens of a device of the present invention, such as a morcellating or other treatment device used to access and treat a fibroid. Shapes on the one or more shaping wires can bias the elongate shaft of the device, such as at a distal portion, to a pre-determined shape. In a preferred embodiment, multiple shaping wires with varied shapes are provided to accommodate different procedures and/or access to different anatomical locations.

Numerous devices of the present invention include an elongate shaft, similar in construction to shafts used in laparoscopic and percutaneous devices. The shafts may be manufactured in a "lay up" process including multiple layers of similar or dissimilar materials, such as layers of flexible biocompatible material separated by a braided material such as metal wire or plastic filament. The construction is chosen to provide adequate column strength and torqueability to access the desired anatomical locations and perform the desired actions. Each shaft preferably has a blunt or otherwise atraumatic distal tip. The shafts may include one or more lumens, such as a lumen configured to slidingly receive an elongate device such as a treatment catheter or guidewire, a lumen configured to allow fluid delivery and/or fluid sampling or removal; an inflation lumen configured to allow inflation of a balloon; a mechanical linkage lumen configured to slidingly receive a cable such as to transmit force through the shaft (e.g. from a lever on a handle on the proximal end of the shaft); a lumen configured to slidingly receive a shaping wire of the present invention; other lumens and combinations thereof.

The elongate shafts of the present invention may include a reinforced section such as a section located at the portion of the shaft that, when inserted into the body, is in proximity to the cervix. The reinforced section can provide the function of preventing collapse of an internal lumen of the shaft (enhanced radial strength) as well as prevent undesired perforation out of the shaft and into tissue such as cervical tissue. The reinforced section may comprise the braiding process described hereabove, and may be provided along a majority of length of the shaft, or a small portion. The shaft may include variable stiffness along its length, and may allow the stiffness to be adjusted, such as through the insertion of a stiffening wire, or by pressurizing an internal (blind) lumen of the shaft. The shaft may include along its length one or more clinician inflatable balloons, such as compliant or non-compliant nylon or PET balloons configured to dilate, deflect the device or neighboring tissue; deliver a drug; or perform another function. The elongate shafts of the present invention are typically less than 9 mm in diameter, and preferably between 5 to 8 mm in diameter, and more preferably between 2 and 5 mm in diameter.

The elongate shafts of the present invention may include clinician controlled deflection means, preferably one or more pull wires attached at their proximal end to a control in a handle on the proximal end of the shaft, and attached on their distal end to a portion of the shaft, such as a distal portion of the shaft. Advancement and retraction of the pull wire causes a portion of the shaft to deflect, such as to bring a treatment element of the present invention in proximity to tissue to be treated. The shafts may further include one or more internal conduits, such as wires or optical fibers which do not need to be advanced or retracted. These conduits may be embedded in the wall of the shaft, fixed to an internal lumen, or sandwiched between to layers present in a layered construction. Wires can be used to transmit electrical signals or energy, in either direction in the shaft. Fiber optic cables can be used to transmit light energy (e.g. laser energy) or signals (e.g. images from a lens), in either direction in the shaft. In the preferred embodiment, the shafts of the present invention include a handle on their proximal end, and the handle includes on or more controls to activate one or more portions of the device. In another preferred embodiment, a "kill-switch" control is included to allow the clinician to quickly stop an ongoing action.

The shafts and other components of the devices of the present invention are constructed of biocompatible materials. The devices may be configured for one-time use or be resterilizable. The materials include medical grade metals, plastics and other materials. Shaped memory metals such as Nitinol and shaped memory polymers may be used to provide controllable material properties or meet specific elasticity and/or resiliency requirements. The shafts and other components may include one or more coatings, such as coatings selected from the group consisting of: anti-infective drugs, anti-thrombogenic drugs; clotting agents; chemotherapeutics; anesthetics such as lidocaine; other drugs; and combinations thereof. Alternatively, the shafts and other components may include drug delivery means, such as drug reservoirs (e.g. connected to a supply of drug internal or external to the device) or drug depots (e.g. containing a supply of drug) One or more markers may be integral to a component of the device, such as a marker selected from the group consisting of: visible and non-visible markers; radiopaque markers; magnetic markers; ultrasonically reflective markers; and combinations thereof.

A functional element may be mounted to the shafts or other components of the devices of the present invention. These functional elements may include a sensor or transducer and/or another functional element such as a camera or marker as described hereabove. Applicable sensors include but are not limited to: electrodes such as electrical mapping electrodes; temperature sensors; pressure sensors; strain gauges; accelerometers; force sensing resistors; position sensors such as linear or rotary encoders; magnetic sensors such as hall effect transistors; optical sensors such as phototransistors; physiologic sensors such as EKG; EEG; respiration; blood sensors such as a blood gas sensors such as an O2 saturation sensors; glucose sensors; blood pressure sensors; pH sensors; other physiologic sensors; and combinations thereof. Applicable transducers include but are not limited to: magnets; electrodes such as radiofrequency electrodes; heat generators; cryogenic generators; force or space-occupying generators such as an expandable balloon or solenoid; drug delivery elements such as iontophoretic elements; sound transducers such as acoustic transducers, ultrasound transducers and subsonic transducers; radiation sources; light sources such as visible or infrared light sources configured to provide a beacon for navigation and ultraviolet light sources configured to treat infection or kill bacteria; visualization elements such as cameras, lenses, fiber optics and ultrasound crystals; other functional elements; and combinations thereof. Functional elements may further include elements to cause dissection of tissue, such as blunt dissection projections and fluid jets.

The systems, methods, apparatus and devices of the present invention are applicable to patients with one or more of the following conditions:

presence of fibroids, polyps, tumors, blood clots or other undesired tissue (e.g. fibroids attached to the wall of the uterus, in the uteral wall or on the outside of the uterus);

endometriosis and other abnormal bleeding;

uteral prolapse;

ectopic pregnancy;

fertility issues (e.g. inability to conceive or desire to avoid pregnancy);

cancer such as carcinoma of the cervix or uterus;

infection;

pain;

and other disorders.

The systems, methods, apparatus and devices of the present invention are applicable to performing one or more therapeutic or diagnostic gynecologic and urologic procedures. These procedures may be performed inside or outside the uterus. Applicable primary procedures include but are not limited to:

fibroid, poly, tumor, blood clot, biopsy and other tissue removal, treatment or denaturing (e.g. removal, treatment or denaturing via mechanical means such as cutting, morcellating, lysing, excising or scraping; ablation such as radiofrequency, laser or cryogenic ablation; and/or removal of blood supply such as via associated vascular occlusion);

fertility procedures (e.g. in-vivo fertilization; tubal opening; egg harvesting and sperm delivery);

sterilization procedures (e.g. fallopian tube occlusion such as internal or external occlusion of the fallopian tube; procedures which detect and/or confirm fallopian tube occlusion; and fallopian tube removal or partial removal);

endometrial ablation or resection (e.g. providing a tamponade force; delivering a clotting or other agent; delivering a fluid such as a fluid at an elevated temperature; providing ablation energy such as radiofrequency; ultrasonic, laser or cryogenic energy);

vascular modification (e.g. procedures that change blood flow such as flow reducing or increasing procedures including vascular stenting and occlusion)

intra-abdominal procedures (e.g. oophorectomy; tubal ligation; tubal resection; endometrial ablation; subserosal fibroid removal and ovarian cyst removal) and drug delivery (e.g. delivery of anesthetics; clotting agents; chemotherapeutics;

occlusive agents, bulking agents and other agents).

In the performance of one or more gynecologic and urologic procedures, such as one or more of the procedures listed above, the systems, methods, apparatus and devices of the present invention may be used to perform one or more additional procedures, including but not limited to:

mechanical or gel distension of organs (e.g. bladder, lung, stomach, bowel, esophagus, oral cavity, rectum, nasal sinus, Eustachian tubes, heart, gall bladder, artery, vein, ducts)

administering of anesthetics (e.g. lidocaine injections proximate the cervix, vaginal wall or other tissue; and injections to otherwise reduce pain associated with cervical dilation; fallopian tube manipulation and vaginal wall penetration)

administering of a muscle relaxant, cervical pre-dilation and softening (e.g. a procedure performed a day or more in advance of a subsequent gynecological procedure)

dilation (e.g. cervical dilation and dilation of a penetration tract through the vaginal wall)

tissue dissection (e.g. blunt dissection; liquid-jet (e.g. saline) dissection; and energy assisted dissection; and dissection utilizing Tumescent solution comprising an anesthetic such as lidocaine and a vasoconstrictor such as epinephrine in order to dissect along normal facial planes and reduce nerve damage)

vaginal wall and other conduit or organ penetration (e.g. penetration comprising an penetrating needle and guidewire passed through the needle)

vessel occlusion or constriction (e.g. occlusion or constriction of a blood vessel such as the uteral artery; a fallopian tube; or the urethra)

implant delivery (e.g. an occlusive device such as occlusive intra-luminal material or a vessel clip; a drug delivery implant such as a drug-loaded gel or foam; a radioactive seed; or suture)

radiation treatment (e.g. temporary or permanent implantation of a radioactive seed or other source of radiation such as a liquid radionucleotide)

delivery of energy (e.g. electromagnetic energy such as radiofrequency energy; chemical energy; heat or cooling energy; mechanical energy such as vibrational energy; sound energy such as subsonic, acoustic and ultrasound energies; radiation; and combinations thereof)

visualization of internal anatomy (e.g. via an endoscope or a camera or lens integral to a device shaft) and guidance of one or more devices (e.g. via a visible beacon such as a light emitted from the uterus, fallopian tubes or other anatomical location or via an electromagnetic beacon such as an antenna receiving a high frequency signal).

The systems, methods, apparatus and devices of the present invention may provide and/or utilize various means and routes of access to an internal location within the patient. Routes of access include but are not limited to:

trans-cervical (defined above);
trans-vaginal-wall (defined above);
trans-uteral (defined above);
trans-vesicle;
trans-urethral;
laparoscopic, and other routes.

The devices and apparatus of the present invention may comprise an elongate shaft that includes one or more lumens such as to slidingly receive one or more separate devices also comprising an elongate shaft. The device lumens may be configured to support over-the-wire insertion over a standard guidewire, or alternatively a side-car mounted near the distal end of the shaft may be provided to support monorail (also known as rapid exchange) insertion. The device lumens, such as the introducer of the present invention, may be sized and be otherwise configured to slidingly receive one or more devices including but not limited to:

treatment device, tissue removal device, subsonic treatment device, drug delivery device, scaffolding device, volume occupying device, stabilizing device, visualization apparatus and navigation apparatus, a shape-modifying wire; all of the present invention;

ablation device;
ligating, lysing and/or excising device;
tissue removing device (e.g. a morcellator; scraper; cutter; or grabber);
tissue cutting device (e.g. an advancable blade cutting device);
tissue dissector (e.g. a blunt dissector; a fluid-jet dissector; or an energy delivery dissector);
suture and knot tying device;
snaring device (e.g. a device used to snare a guidewire or blood clot);
visualization device (e.g. a hysteroscope or other endoscope);
navigation device;
drug delivery device (e.g. a iontophoresis catheter); and
vaginal crossing device (e.g. a needle based device which places a guidewire from inside the vaginal canal and through the vaginal wall).

The device lumens may be sized and include access elements such as luer fittings to attach to drug delivery devices such as syringes and infusion pumps. The device elongate shaft may be sized and otherwise configured to be passed through one or more devices including but not limited to:

dilators (e.g. sequential dilators or balloon dilators), and
sheaths and introducers Reference will now be made in detail to the present embodiments of the invention, examples of which are illustrated in the accompanying drawings. Wherever possible, the same reference numbers will be used throughout the drawings to refer to the same or like parts.

Referring now to FIG. 1, a preferred embodiment of an introducer consistent with an embodiment of the present invention is illustrated. As shown in FIG. 1, introducer 100a includes an elongate, hollow shaft, sheath 110, which is configured to have distal end 111 (preferably with an atraumatic leading edge) be inserted into the body of a patient, such as through the cervix and into the uterus, to provide a working channel to introduce tools through a lumen of sheath 110 and into the uterus. In an alternative embodiment, distal end 111 of sheath 110 is placed into the vaginal opening of a patient, and manipulated to penetrate through the vaginal wall (such as by advancing over a pre-existing guidewire penetrating the vaginal wall), such as to provide a working channel to introduce tools through a lumen of sheath 110 to a location outside the uterus. Sheath 110 may be configured to slidingly receive two or more devices, independently or simultaneously. In an alternative embodiment, sheath 110 includes multiple lumens along its length, each lumen configured to slidingly receive a separate device. Sheath 110 may remain in place throughout the subsequent procedure, or for a portion of the procedural steps. Sheath 110 may be repositioned during the procedure, such as to advance or withdraw sheath 110.

Sheath 110 is manufactured from medical-grade plastics, metals and other biocompatible material such as a sheath including a Teflon outer layer. One or more portions of sheath 110 may be radiopaque, such as by inclusion of a barium sulfate in plastic material or inclusion of one or more metal portions which provide sufficient radiopacity. In a preferred embodiment, distal end 111 includes a radiopaque marker. Sheath 110 is preferably of a braided construction as has been described hereabove, and includes a reinforced portion, reinforcement 115 (e.g. consisting of a metal or plastic braided patch or embedded tube as has been described hereabove) near its distal end, configured to maintain the patency of one or more lumens within sheath 110 when external pressure is exerted (e.g. cervical or vaginal wall pressure) on that portion of sheath 110. Alternatively or additionally, reinforcement 115 may be configured to prevent a device inserted into sheath 110 from inadvertently puncturing out the side of sheath 110, such as to prevent a puncture that would damage cervical or other patient tissue unexpectedly. On the proximal end of sheath 110 is device insertion port 120, which provides access to an internal lumen of sheath 110 and has been configured to maintain fluid stasis with or without a device inserted through it. Port 120 preferably has an "X" cut opening through one or more diaphragms that maintain that fluid seal. The thicknesses of the diaphragms and the materials chosen preferably maintain pressure up to a predetermined level (e.g. 50 mm Hg) after which fluid is automatically evacuated to prevent damage to the patient's internal tissue.

Mechanically attached and in fluid communication with device insertion port 120 are input valve 121 and output valve 122, each of which includes a standard luer connector for attachment to standard fluid infusion lines. Input valve 121 and output valve 122 may include simple one-way valves or more sophisticated valves that open (in either direction or both) at pre-determined pressures. In combination with port 120, fluid infusion and fluid evacuation means (not shown but preferably gravity driven or pump driven fluid movement means), can be attached to port 121 and port 122 and control the level of fluid introduced into the patient via introducer 100a. In a preferred embodiment, sheath 110 is a single lumen and the fluid is introduced through that lumen. In an alternative embodiment, sheath 110 includes multiple lumens and fluid can be delivered or evacuated through one or more lumens, simultaneously or independently. In the various gynecological procedures described herein, a volume of liquid and level of liquid pressure are used to visualize the internal space and/or provide space to manipulate one or more devices. In an alternative embodiment, a gel or gas is delivered into the patient.

Introducer 100a may include a handle, not shown, on its proximal end. The handle may include one or more controls, as has been described hereabove. Sheath 110 may include one or more valves within one or more lumens of sheath 110, such as a valve near the distal end 111. Introducer 100a may include a balloon along sheath 110, such as a balloon configured to dilate tissue such as the cervix or the vaginal wall. In an alternative embodiment, multiple balloons are employed, such as a balloon on a balloon configuration. Each balloon integrated into sheath 110 may have an integrally mounted functional element, as has been described hereabove but preferably a pressure or force sensor used to provide information to the clinician or a system component regarding dilation conditions (reference FIG. 13 herebelow). Sheath 110 may include one or more functional elements along its length, such as a vibrational transducer configured to assist in dilation. Sheath 110 may include a lumen for insertion of a shaped wire, such as a wire configured to resiliently bias sheath 110 and/or a wire configured to place a "straightening" bias on the cervical canal during introducer insertion, once inserted or both. In another alternative embodiment, sheath 110 includes an expandable cage structure, not shown but protruding from distal end 111. The expandable cage structure may have a fluted geometry such as a geometry configured to follow the contour of the uterus when introducer 100a is inserted through the cervix.

Introducer 100 of FIG. 1 and the numerous embodiments of the introducers described throughout this application, are sized to accommodate the one or more devices placed through sheath 110, while remaining as small as possible to reduce tissue trauma and pain to the patient, especially when sheath 110 is placed through the cervix of a patient. In a first embodiment, sheath 110 of Introducer 100 is typically less than 9 mm in diameter and preferably less than 8 mm diameter. In another embodiment, sheath 110 is less than 7 mm in diameter. In another embodiment, sheath 110 is less than 6 mm in diameter. In another embodiment, sheath 110 is less than 5 mm in diameter. In another embodiment, sheath 110 is less than 4 mm in diameter. In another embodiment, sheath 110 is less than 3 mm in diameter. In another embodiment, sheath 110 is less than 2 mm in diameter. Sheath 110 is configured in size and rigidity to prevent painful and potentially destructive dilation of the cervix.

Figure 1A:
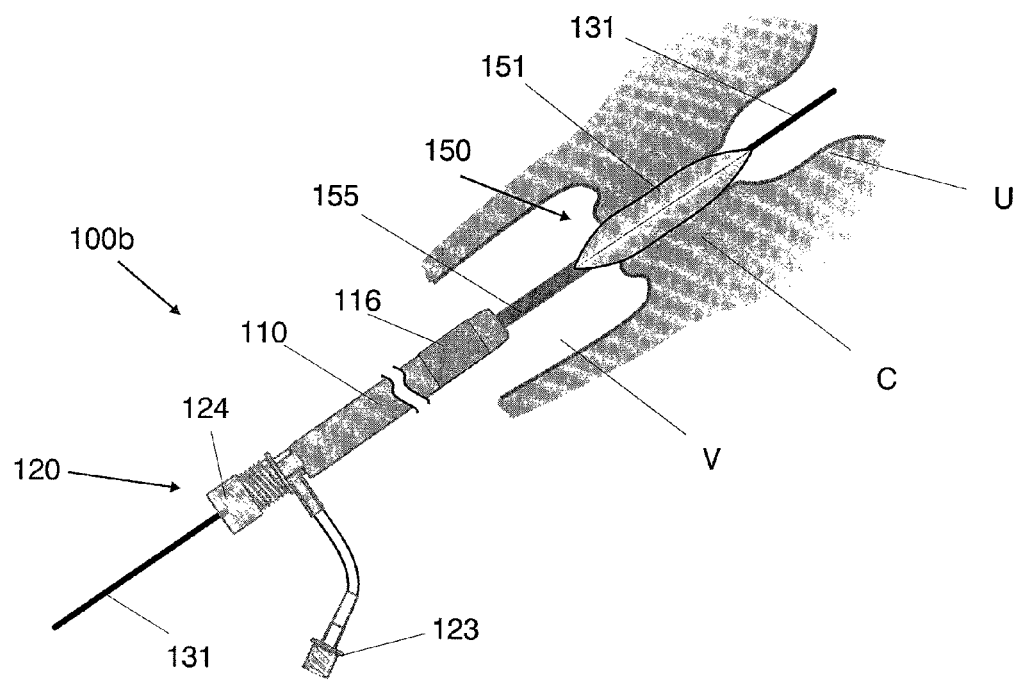
FIG. 1A illustrates a side sectional view of another exemplary embodiment of an introducer consistent with the present invention, wherein the introducer includes a pre-dilating balloon and is shown being deployed in the cervix of a patient.

Referring now to FIG. 1A, another preferred embodiment of an introducer consistent with the present invention is illustrated. Introducer 100b has a dual balloon construction and includes sheath 110, of similar construction to sheath 110 of FIG. 1. Introducer 100b is shown over a guidewire 131, such as an 0.038" standard interventional guidewire, which has been advanced through vagina V, through cervix C and into uterus U. An inflatable balloon introducer assembly 150 includes balloon 151 and shaft 150 and is shown having been advanced into the cervix C of a patient and balloon 151 inflated (inflation lumen and inflation port not shown). Inflation of balloon 151 is used to pre-dilate cervix C such that sheath 110 can be advanced into cervix C. Inflation balloon 151 is preferably less than 9 mm in diameter when fully inflated, and more preferably between 2 and 8 mm in diameter. Shaft 155, which is slidingly received by sheath 110, may be pulled back prior to advancement of sheath 110, or balloon 151 may be left in place, although preferably partially deflated prior to advancement. In an alternative embodiment, balloon assembly 150 including shaft 155 and balloon 151 may be configured to be completely removed from sheath 110 such as after sheath 110 is placed to its desired location in the patient's body. After advancement of sheath 110, further dilation of the cervix may be accomplished by subsequent inflation of balloon 151, and/or via inflation of a balloon integral to sheath 110, balloon 116 (inflation lumen and inflation port also not shown). Inflation of either balloon 151 or balloon 116, or both, may be used to anchor sheath 110 in place.

On the proximal end of sheath 110 is device insertion port 120, which provides access to an internal lumen of sheath 110 and is in fluid communication with fluid transfer port 123 configured to introduce and/or remove fluid or other media through sheath 110 and into the patient as has been described hereabove. Port 120 includes a rotating collar 124, which can be rotated to permit devices to pass through port 120 as well as seal around those devices, such as via a diaphragm which seals around inserted devices similar to a Tuohy Borst valve configuration. Port 120 further provides fluid stasis when no device is inserted through it.

Guidewire 131 may be replaced with a different guidewire, such as with a guidewire with different stiffness or lubricious properties. Guidewire 131 may remain in place for a majority of the procedure, or may be removed early on.

Figure 1B:
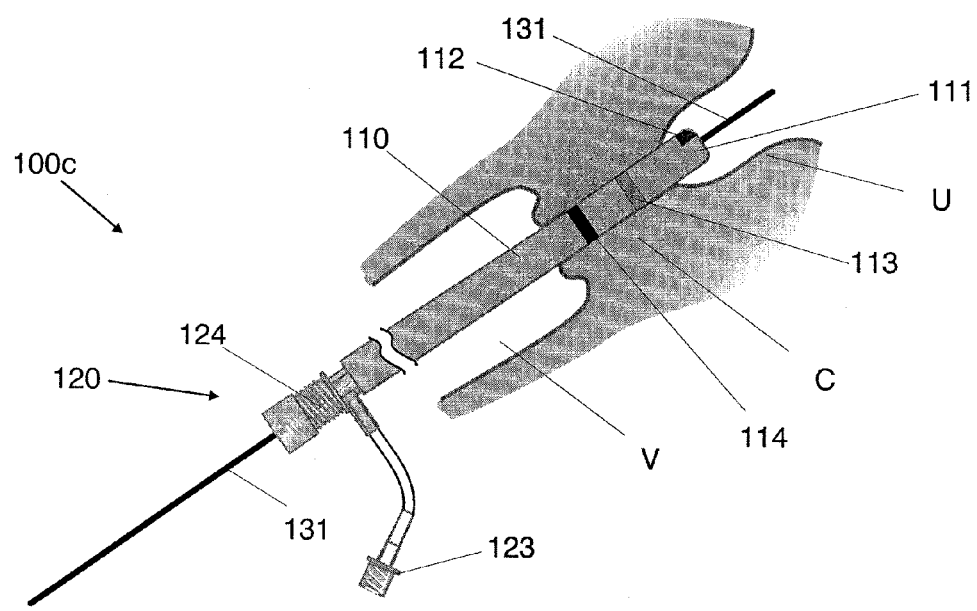
FIG. 1B illustrates a side sectional view of another exemplary embodiment of an introducer consistent with the present invention, wherein the introducer includes a drug delivery element and a strain gauge and is shown deployed in the cervix of a patient.

Referring now to FIG. 1B, another preferred embodiment of an introducer consistent with the present invention is illustrated. Introducer 100c includes sheath 110 with distal end 111, device insertion port 120 with rotating collar 124 and fluid transfer port 123, all of similar construction to similar components of introducer 100a of FIG. 1 and introducer 100b of FIG. 2. Introducer 100c has been placed over guidewire 141 and advanced such that its distal portion resides within cervix C and its distal end is within uterus U of a patient.

Introducer 100c includes a force measuring element, strain gauge 113, which is used to monitor forces exerted on sheath 110 (and the corresponding resultant forces exerted on the neighboring tissue). Wires, not shown but attached to strain gauge 113 and traveling proximally through sheath 110, attach to an electronic module, also not shown, and provide pressure or other force information to the clinician or a system component which processes the information.

Introducer 100c further includes drug delivery element 114, such as a drug delivery mechanism. Drug delivery element 114 may be a simple drug coating, or may be a depot that stores a drug such as an anesthetic and delivers the drug via osmosis, iontophoresis or other drug delivery mechanism. In a preferred embodiment, drug delivery element 114 is a pressure releasable sack, such as a sack with a duck bill valve, and when sufficient pressure is applied to the sac, such as via the cervix, a drug, such as lidocaine, is delivered. In another preferred embodiment, drug delivery element 114 includes multiple pressure-driven sacks, such as multiple sacks in different locations and/or multiple sacks with different delivery pressure properties.

Introducer 100c further includes a visualization apparatus, visualization element 112 preferably a forward looking visualization tool such as forward looking ultrasound, or a lens that provides an image to a camera, not shown, but preferably a camera system that receives an image from a fiber optic in optical communication with the lens. A display, not shown but preferably integrated into a laptop computer via a USB or video connection, provides the camera image to the clinician and/or patient.

Referring now to FIG. 2, a preferred embodiment of a system 10 consistent with the present invention is illustrated. System 10 includes introducer 100d and tissue removal device 200 which includes an integral visualization apparatus, camera 256 mounted to side-saddle catheter 250. Introducer 100d includes sheath 110, device insertion port 120 and fluid transfer port 123, all of similar construction to similar components of introducers 100a, 100b and 100c hereabove. Introducer 100d has been placed and advanced such that its distal portion resides within cervix C and its distal end provides access within uterus U of a patient. Sheath 110 includes a marker, radiopaque ring 117 which can be used by the clinician to determine and/or confirm with fluoroscopy the diameter (e.g. the inside diameter) of sheath 110 at the location of ring 117, such as to confirm or rule out the condition where the cervix may be undesirably compressing sheath 110. In an alternative embodiment, ring 117 is an ultrasonically reflective marker enabling the condition to determine the associated diameter by using ultrasound, such as via an ultrasound device commonly located in a gynecologist office.

Tissue removal device 200, a morcellating device, has been advanced through port 120, through a lumen of sheath 110, and into the uterus U of a patient. Tissue removal device 200 includes an elongate shaft, tube 201, which includes on its distal end 203 a cutout, window 202. A cutting element 210 is present within window 202 such that as the distal end of tube 201 is manipulated near tissue, cutting element 210 will cut that tissue. Vacuum means, not shown put in fluid communication with a lumen of tube 201 and window 202, evacuate the pulverized, cut or otherwise detached particles to a location outside of the patient. In a preferred embodiment, vacuum and evacuation means are integral to a handle of device 200. In another preferred embodiment, vacuum and evacuation means are connected to a port which is integral to a handle of device 200. Cutting element 210, of one or more configurations such as the configurations described below in reference to FIGS. 2A and 2B, is preferably attached to a speed control mechanism, not shown. The speed control mechanism is simplified for use by including one or more feedback means (e.g. electromotive feedback, rotation or other speed feedback, vibrational feedback, physiologic feedback such as EKG or blood pressure, or other feedback), wherein the feedback means can be used to automatically control the speed, greatly simplifying use for the clinician. In a preferred embodiment, the clinician available feedback is limited to a small number of finite settings, such as less than 10 settings. In another preferred embodiment, a kill-switch is included on a handle of the device, which is readily accessible to the clinician and upon activation removes power and/or applies a breaking function to instantaneously stop the cutting motion.

Referring additionally to FIG. 2C, also included in the system 10 of FIG. 2 is a side-saddle catheter 250 which includes sleeve 252 (e.g. a Teflon sleeve) which slidingly surrounds tube 201. Advancement and retraction of an elongate shaft, shaft 205 causes a visualization apparatus, camera 255 to be correspondingly advanced and retracted relative to tube 201. The image received from camera 255, such as an image displayed on a laptop computer display as has been described hereabove, is used by the clinician to position the window 202 of tissue removal device 200 near one or more fibroids, such as fibroid F1 located within the wall of uterus U and fibroid F2 attached to the wall of uterus U. Camera 225 may utilize CCD and/or MEMS mirror control technology to produce and/or transfer an image. In a preferred embodiment, camera 225 includes one or more motion sensing elements, such as miniaturized accelerometers or gyros which can be fed back to an image processing system, not shown but preferably external to the patient, such that the image provided to the clinician does not move as the camera is moved. Alternatively or additionally, side saddle catheter 250 includes one or more functional elements, not shown but preferably selected from the list of functional elements provided hereabove. The functional element may be a fluid delivery port, such as a port configured to deliver saline or other clear fluid to clear the pathway of the camera view or to clean off a contaminated lens.

Referring now to FIG. 2A, a preferred embodiment of the cutting element 210 of FIG. 2 is shown. The distal end of tube 201 and window 202 is shown with an oscillating cutter 211 attached to an elongate control linkage, shaft 221, which is attached at its proximal end to a reciprocating motor assembly, not shown, but preferably a simplified, precision speed controlled assembly as has been described hereabove. In a preferred embodiment, the speed assembly utilizes feedback, also as has been described hereabove. Referring now to FIG. 2B, another preferred embodiment of the cutting element of FIG. 2 is shown. The distal end of tube 201 and window 202 is shown with an spinning or rotational cutter 212 attached to an elongate control linkage, shaft 221, which is attached at its proximal end to a rotational motor assembly, not shown, but preferably a simplified, precision speed controlled assembly as has been described hereabove. In a preferred embodiment, the speed assembly utilizes feedback, also as has been described hereabove.

System 10 of FIG. 2 is configured such that the outer diameter of sheath 110 of introducer 100d is minimized. Inserted devices such as tissue removal device 200 (including camera 256) and other inserted devices are also minimized in the cross sectional profiles of their distal portions, such that the inner diameter (and thus the outer diameter) of sheath 110 can be reduced. In a first embodiment, sheath 110 of Introducer 100 is typically less than 9 mm in diameter and preferably less than 8 mm diameter. In another embodiment, sheath 110 is less than 7 mm in diameter. In another embodiment, sheath 110 is less than 6 mm in diameter. In another embodiment, sheath 110 is less than 5 mm in diameter. In another embodiment, sheath 110 is less than 4 mm in diameter. In another embodiment, sheath 110 is less than 3 mm in diameter. In another embodiment, sheath 110 is less than 2 mm in diameter. Sheath 110 is configured in size and rigidity to prevent painful and potentially destructive dilation of the cervix.

Figure 3:
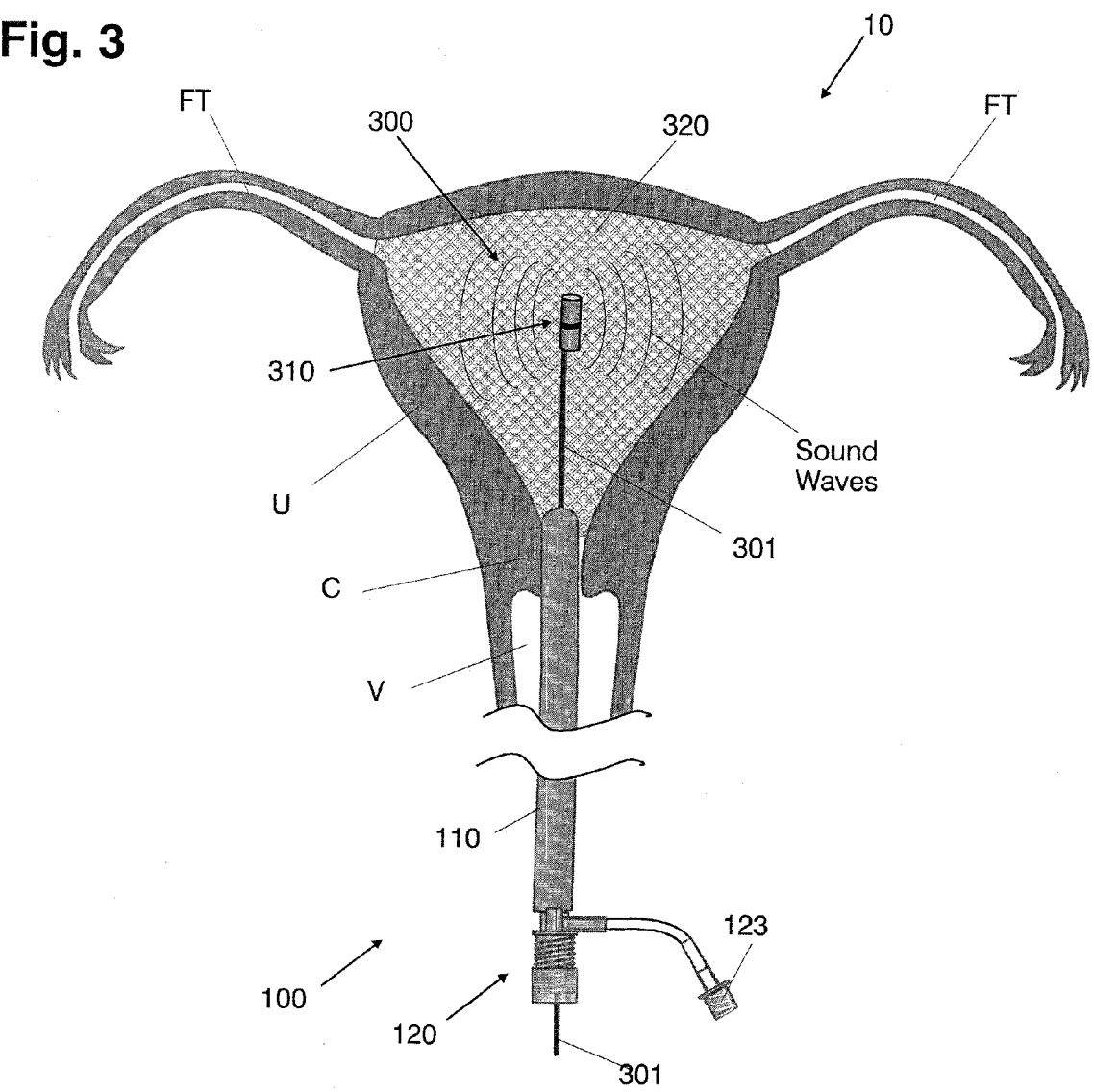
FIG. 3 illustrates a side sectional view of another exemplary embodiment of a system consistent with the present invention, wherein an introducer is shown deployed in the cervix of a patient, and a subsonic treatment device has been advanced through the introducer and into the uterus.

Referring now to FIG. 3, another preferred embodiment of a system 10 consistent with the present invention is illustrated. System 10 includes introducer 100 and subsonic treatment device 300. Introducer 100 includes sheath 110, device insertion port 120 and fluid transfer port 123, all of similar construction to similar components of introducers 100a, 100b, 100c and 100d hereabove. Introducer 100d has been placed and advanced such that its distal portion resides within cervix C and its distal end provides access within uterus U of a patient. A treatment catheter of the present invention, acoustic generator device 300 has been inserted through port 120, down a lumen of sheath 110 and into the uterus of the patient.

Figure 3A:
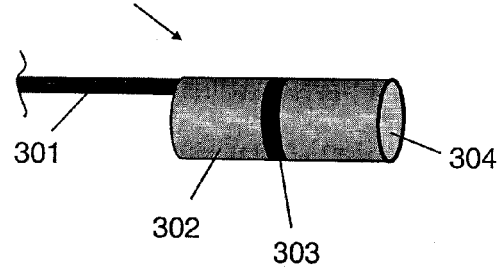
FIG. 3A illustrates a side view of the distal end of the subsonic treatment device of FIG. 3.

Referring additionally to FIG. 3A, acoustic generator device 300 includes acoustic transducer 310 which comprises housing 302, preferably a metal can with a lumen 304, and a sound crystal 303, configured to deliver subsonic sound waves. System 10 preferably includes specialized fluid medium, which is injected into uterus U via port 123 and sheath 110. The fluid medium is configured to adequately conduct the emitted sound waves and provide an impedance mismatch between it and the targeted tissue (e.g. endometrium), such that large amounts of energy (sufficient to destroy or otherwise denature the tissue cells) is transferred to the tissue when the subsonic waves arrive at the interface.

Figure 4:
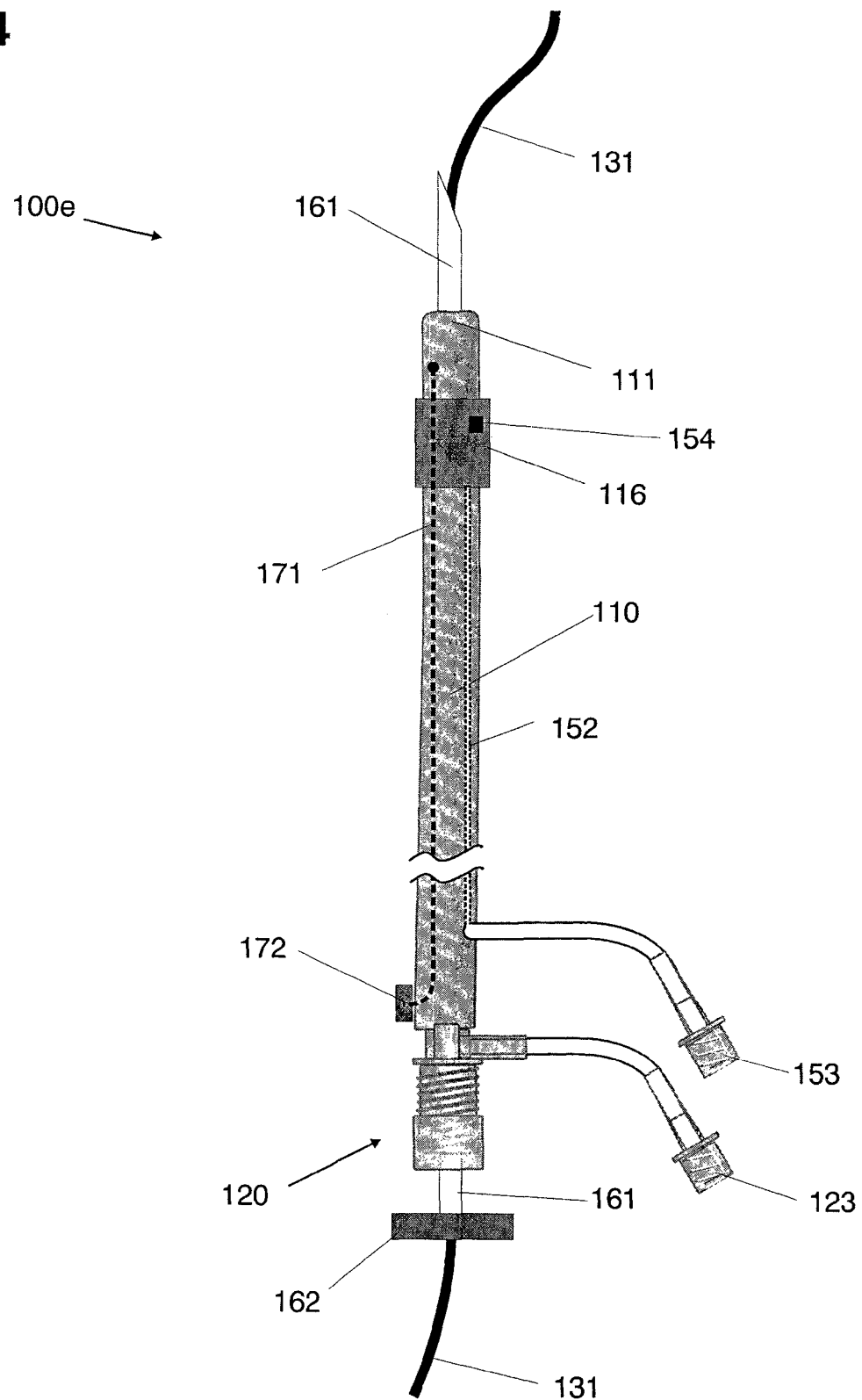
FIG. 4 illustrates a side view of another exemplary embodiment of an introducer consistent with the present invention, wherein the introducer includes a removable needle assembly and an inflatable balloon near its distal end.

Referring now to FIG. 4, another preferred embodiment of an introducer consistent with the present invention is illustrated. Introducer 100e is configured to puncture through tissue, such as the vaginal wall to perform a trans-vaginal-wall procedure. Introducer 100e includes sheath 110 with balloon 116 and distal end 111, device insertion port 120 and fluid transfer port 123, all of similar construction to similar components of introducer 100a, 100b, 100c and 100d hereabove.

Balloon 116, which can be configured to perform one or more functions such as to dilate tissue, to anchor sheath 110 in place and to maintain one or more lumens of sheath 110 in an open state under high loading conditions. Balloon 116 is in fluid communication with inflation lumen 152 and injection port 153 such that a syringe or endoflator attached to the luer of port 153 can be used to inflate balloon 116. Balloon 116 includes a miniaturized, integral pressure sensor 154, which is preferably attached to one or more wires, not shown but traveling proximally and attaching to an electronic module which processes the received signal and provides pressure information to the clinician and/or utilizes the information in one or more ways such as to reduce patient pain such as via the "smart" dilation system and method described in detail in reference to FIG. 13 hereBelow. Additional balloons and/or pressure sensors may be integrated into sheath 110.

Pull wire 171 is fixedly attached at its distal end to a distal portion of sheath 110, and it is operably attached at its proximal end to knob 172, such that rotation of knob 172 causes sheath 170 to deflect. As shown in FIG. 4, rotation of knob 172 that causes pull wire 172 to retract causes the distal end of sheath 110 to deflect to the left and rotation of knob 172 that causes pull wire 172 to advance causes sheath 110 to deflect to the right. In an alternative embodiment, additional one or more pull wires are included to allow a clinician to deflect sheath 110 in multiple directions at multiple points along the length of sheath 110. Deflection of sheath 110 allows for directional orientation, positioning and advancement of the one or more treatment or other devices that can be inserted into sheath 110 via port 120 (inserted devices not shown).

Introducer 100e includes a tissue penetrating assembly comprising needle 161, an elongate hollow needle preferably constructed of stainless steel or Nitinol, which has fixedly attached on its proximal end, knob 162. Needle 161 resides within a lumen of sheath 110, and is in place when introducer 100e is advanced through tissue. Needle 161 has an internal lumen sized to slidingly receive guidewire 131. Guidewire 131 can be placed trough needle 161 after needle 161 has been advanced through tissue (guidewire loaded from proximal end of needle 161). Alternatively, guidewire 131 can be placed to a target location, such as through the vaginal wall of a patient via another needle device, and then passed through needle 161 (guidewire loaded from distal end of needle 161). In a preferred embodiment, needle 161 can be used to deliver anesthetic to tissue prior to needle 161 and/or sheath 110 advancement.

Introducer 100e may have one ore more functional elements, such as a functional element described hereabove and integrated into sheath 110. In a preferred embodiment, a functional element comprising a visualization apparatus or a portion of a visualization apparatus, such as a camera lens and fiber optic or an ultrasound crystal and associated wiring are contained within sheath 110. Advancement of sheath 110e, such as through the vaginal wall to a location neighboring the outside of a patient's uterus, may require dissection of tissue. In a preferred embodiment, introducer 100e includes a functional element such as a blunt dissector, a fluid jet, or other dissection element. In another preferred embodiment, a blunt dissection device, such as a blunt tipped probe, electrocautery probe, or fluid-jet probe, is advanced through a lumen of sheath 110 prior to and/or during advancement of sheath 110 through tissue. Once inserted into the body of the patient, the distal portion of sheath 110 may need to be tracked, such as it is advanced through the vaginal wall at the preferred location of the anterior or posterior culdesac of the vagina, to a location outside the uterus. Tracking means, such as visualization systems and navigation systems of the present invention, may be used such as by incorporating one or more visualization or navigation elements in introducer 100e and/or by using separate devices to navigate and/or visualize. In a preferred embodiment, a visible light source is placed in a fallopian tube and a camera integral to introducer 100e or a device inserted through sheath 110 is used to locate the visible light source and access the associated fallopian tube. In another preferred embodiment, an electromagnetic transmitting antenna is placed in a fallopian tube and a receiving antenna is integral to introducer 100e or a device inserted through sheath 110 and is used to locate the transmitting source and access the associated fallopian tube.

Figure 5:
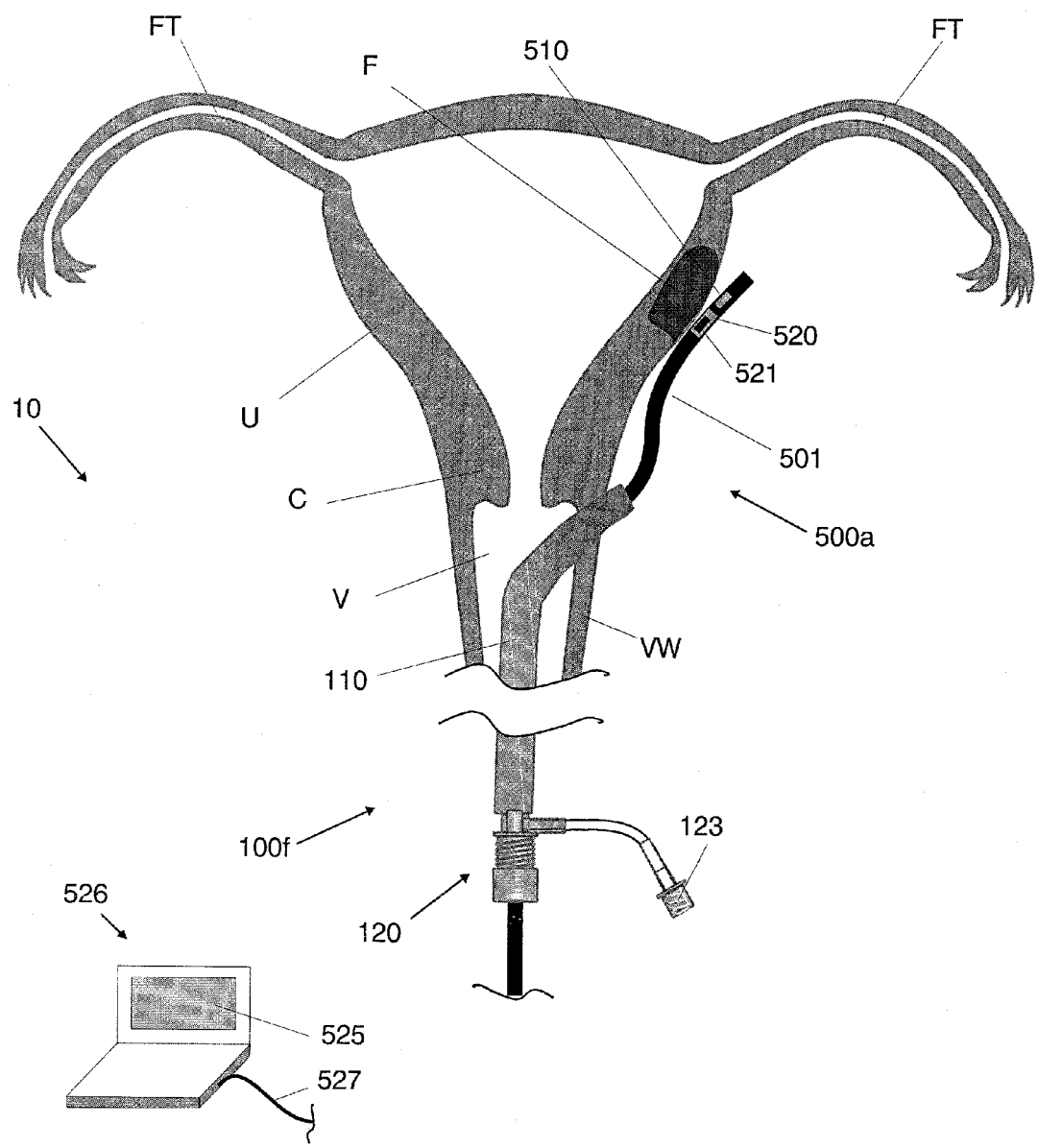
FIG. 5 illustrates a side sectional view of another exemplary embodiment of a system consistent with the present invention, wherein an introducer is shown deployed through the vaginal wall of a patient and a treatment device has been advanced through the introducer to a location outside the uterus and proximate a fibroid in the uteral wall.

Referring now to FIG. 5, another preferred embodiment of a system 10 consistent with the present invention is illustrated. System 10 includes introducer 100f and treatment catheter 500a which includes visualization element 520 and orientation apparatus 521. Introducer 100f includes sheath 110, device insertion port 120 and fluid transfer port 123, all of similar construction to similar components of introducers 100a, 100b, 100c, 100d and 100e hereabove. Introducer 100f has been advanced through the vaginal opening into the vagina V of a patient, to a distal location of the vaginal canal, proximate the cervix C. Sheath 110 has exited through the vaginal wall, as was described hereabove in reference to FIG. 4. A treatment or diagnostic device, as have been described in detail hereabove, treatment catheter 500a, has been advanced through a lumen of sheath 110, and further advanced, such as with manipulation via pull wires integral to introducer 100f and/or treatment catheter 500a, neither pull wires shown, such that the distal end of treatment catheter 500a is proximate a fibroid F located in the wall of uterus U.

Treatment catheter 500a includes shaft 501, which includes near its distal end treatment element 510, such as a morcellating assembly, a subsonic generator, an excisor, a cutter, an ablation element, or other tissue removal or denaturing element as has been described in detail hereabove. Also located near the distal end of shaft 101 is visualization element 520 which is preferably a camera lens connected to a fiber optic cable and configured to produce an image on display 525 of laptop 526 via a cable, wire bundle 527. Alternatively, visualization element 520 is an ultrasound crystal or crystals such as a rotating crystal or phased array of crystals, configured to produce an image on display 525 of laptop 526 via cable 527. Visualization element 520 further includes orientation apparatus 521, a nanoscale mechanism, such as a MEMS gyroscope, accelerometer or series of mercury switches, that is configured to provide movement information to an image processing unit such that the image provided to the clinician does not move as the visualization element moves. The image processing unit may be integral to laptop 526 and/or another component of system 10.

Shaft 501, which extends beyond the proximal end of introducer 100f and exits port 120, preferably includes on its proximal end a handle with one or more clinician controls (e.g. on-off buttons, pull wire rotational knobs, etc) and/or connections such as electrical connections to laptop computer 526, or mechanical connections such as to motor assemblies which provide motion to visualization element 520 (e.g. to a rotating ultrasound crystal) or treatment element 510 (e.g. to a spinning or reciprocating cutting blade).

Anesthetics, such as lidocaine, may be administered peri-procedurally (prior to, during and post procedure), via a separate device, or via one or more functional elements of introducer 100f. Numerous gynecological procedures are applicable to the system 10 and method of FIG. 5, including but not limited to: intra-uteral procedures (re-entering uterus thus avoiding cervical crossing); uteral wall procedures (e.g. the fibroid F treatment shown); fallopian tube procedures (e.g. tubal ligation); ovary procedures (e.g. egg harvesting); cancer treatment procedures; pain treatment procedures; other tissue treatment or removal procedures, and intra-abdominal procedures. As described in reference to FIG. 4, one or more blunt dissection procedures may be performed in the placement of introducer 100f and/or the advancement of one or more devices (e.g. treatment catheter 500a) through sheath 110 and to the target procedure location. Also as described in FIG. 4, one or more navigation or visualization procedures or devices may be used to navigate introducer 100f and/or treatment catheter 500a.

In an alternative embodiment, an additional device is inserted through port 120 and sheath 110, either sequentially or simultaneously with treatment catheter 500a. The additional device may perform one or more functions such as that of a treatment device, navigation device, stabilizing device, visualization device or other device as has been described as performing a function related to the intended gynecologic and urologic procedures described throughout this application. In another alternative embodiment, treatment catheter 500a includes a second treatment element, of similar or dissimilar functionality to treatment element 510.

Figure 5A:
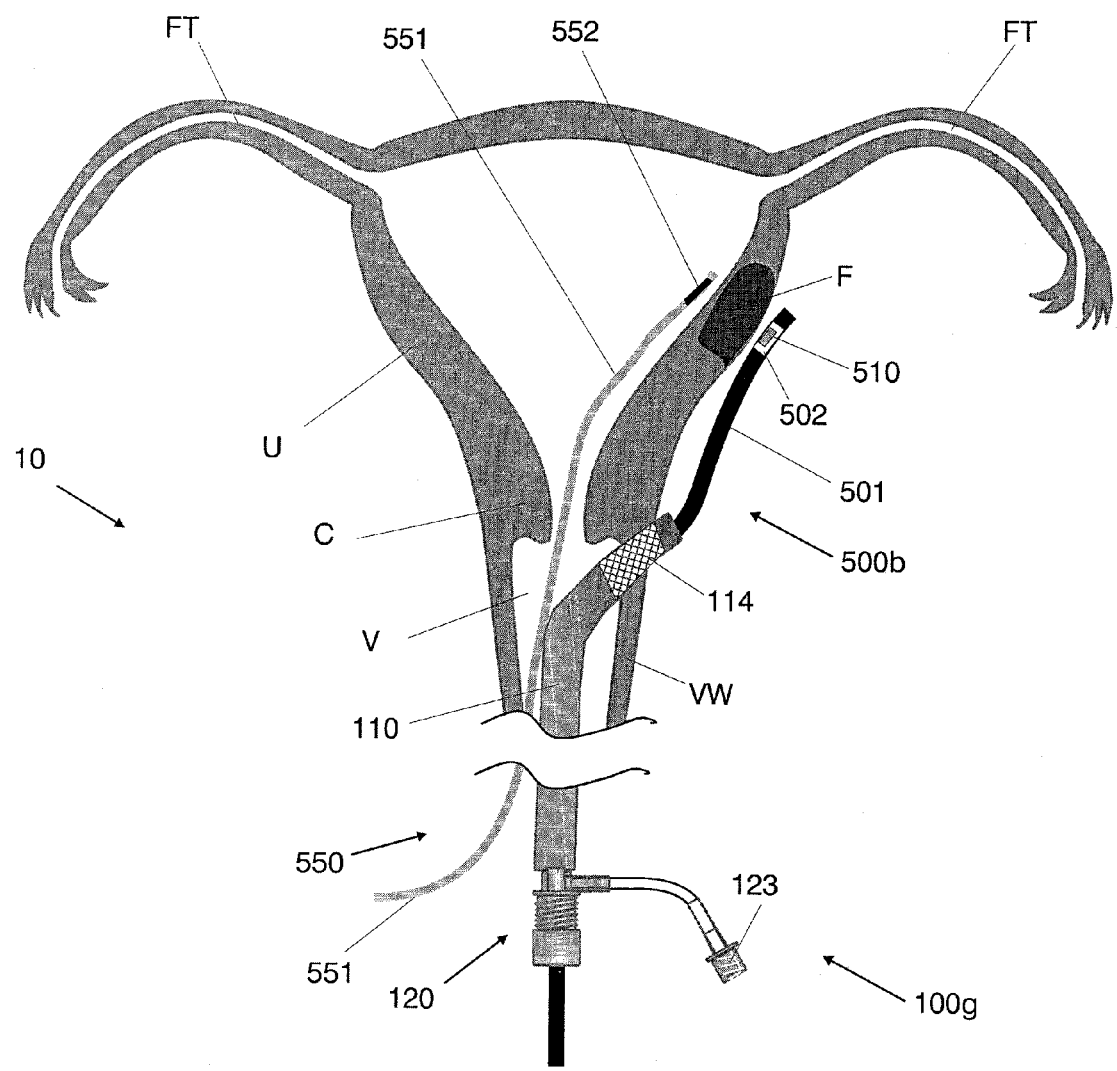
FIG. 5A illustrates a side sectional view of another exemplary embodiment of a system consistent with the present invention, wherein an introducer is shown deployed through the vaginal wall of a patient, a treatment device including a magnet in its distal portion has been advanced through the introducer to a location outside the uterus and a stabilizing magnetic device has been advanced into the uterus proximate a fibroid.

Referring now to FIG. 5A, another preferred embodiment of a system 10 consistent with the present invention is illustrated. System 10 includes introducer 100g, treatment catheter 500b and stabilizing device 550. Introducer 100g includes sheath 110, device insertion port 120 and fluid transfer port 123, all of similar construction to similar components of introducers 100a, 100b, 100c, 100d, 100e and 100f hereabove. Introducer 100g has been advanced through the vaginal opening into the vagina V of a patient, to a distal location of the vaginal canal, proximate the cervix C. Sheath 110 has exited through the vaginal wall, as was described hereabove in reference to FIG. 4. Sheath 110 includes drug delivery element 114, located along sheath 110 at a location proximate the intended vaginal wall crossing, such that one or more drugs, preferably an anesthetic such as lidocaine, can be delivered to reduce pain. Drug delivery element 114 may deliver a drug via simple infusion means such as osmosis or a weak-bonded coating transitioning into solution, or more sophisticated means such as pressure-regulated delivery or iontophoresis as has been described in detail hereabove.

A treatment or diagnostic device, as have been described in detail hereabove, treatment catheter 500b, has been advanced through a lumen of sheath 110, and further advanced, such as with manipulation via pull wires integral to introducer 100f and/or treatment catheter 500b, neither pull wires shown, such that the distal end of treatment catheter 500b is proximate a fibroid F located in the wall of uterus U. Treatment catheter 500b includes shaft 501, which includes near its distal end treatment element 510, such as a morcellating assembly, a subsonic generator, an excisor, a cutter, an ablation element, or other tissue removal or denaturing element as has been described in detail hereabove. Also located near the distal end of shaft 101 is magnet 502, such as a rare earth magnet or clinician activatable electromagnet configured to allow the distal portion of shaft 501 of catheter 502 to be manipulated by one or more clinician-controllable magnetic fields. System 10 further includes stabilizing device 550, inserted into the uterus through the vagina V and cervix C of the patient (outside of introducer 100g). At the distal end of shaft 551 of stabilizing device 500 is a second magnet, magnet 552, preferably a rare earth magnet or clinician activatable electromagnet similar or dissimilar (such as a difference in size and/or magnetic field strength) to magnet 502 of treatment catheter 550b. Manipulation of the distal ends of either or both stabilizing device 550 or treatment catheter 500b such that magnet 552 is in relative proximity to magnet 502 will enable the magnetic force to pull the two magnets and associated distal ends together. In a preferred embodiment, either or both magnet 552 and magnet 502 are electromagnets such that one or both magnetic fields can be deactivated for initial manipulation(s), and activated to achieve final position, such as at a location where treatment element 510 is in close proximity to uteral fibroid F, as shown in FIG. 5A. In a preferred embodiment, the magnetically guided system 10 of FIG. 5a can perform one or more procedures without the need for a camera or other visualization apparatus. In an alternative embodiment, a camera or other visualization apparatus is used, such as with a visualization element incorporated into sheath 100g, treatment catheter 500b or stabilizing device 550.

Shaft 501, which extends beyond the proximal end of introducer 100g and exits port 120, and shaft 551 both preferably include on their proximal end a handle with one or more clinician controls (e.g. on-off buttons, pull wire rotational knobs, etc) and/or connections such as electrical connections to a laptop computer (not shown but similar to laptop computer 526 of FIG. 5), or mechanical connections such as to motor assemblies which provide motion to treatment element 510 (e.g. to a spinning or reciprocating cutting blade) or to manipulate one or more internal pull wires such as to create a robotically manipulated system.

Figure 6:
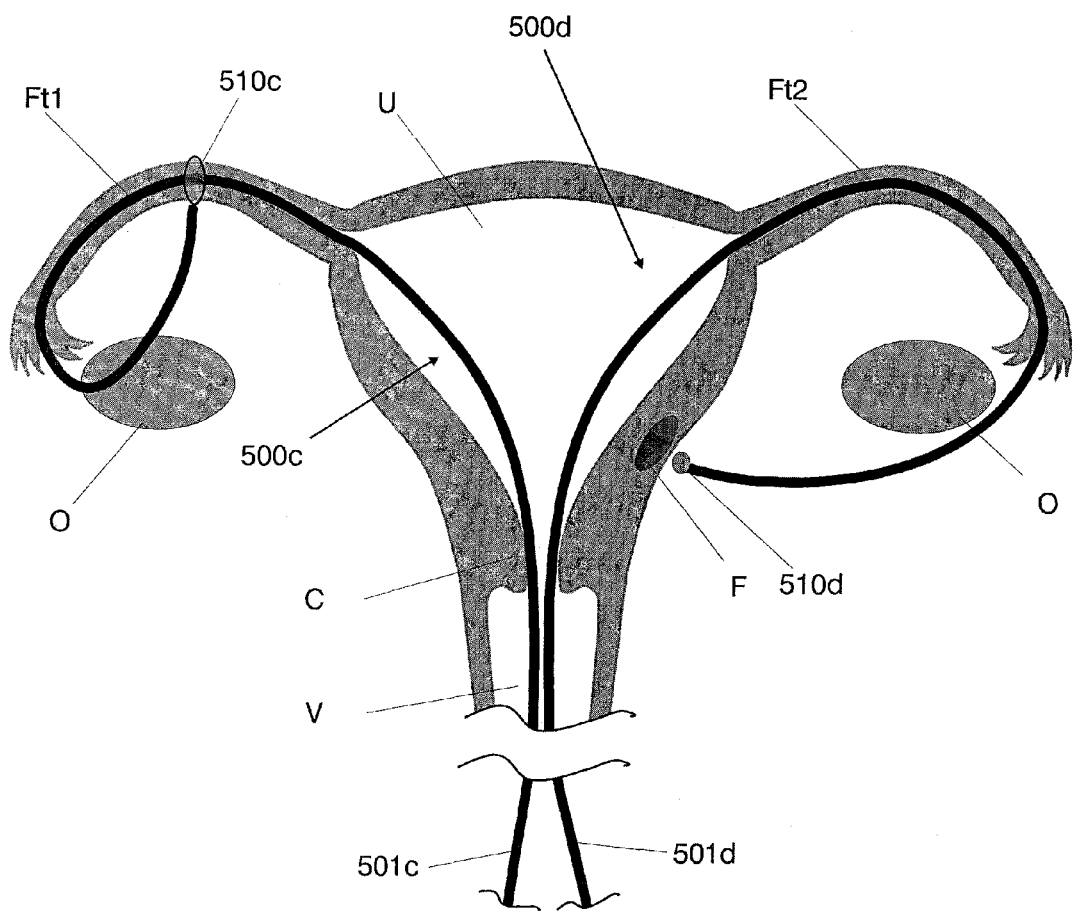
FIG. 6 illustrates a side sectional view of an exemplary method consistent with the present invention, wherein a first treatment device has been advanced through the cervix and a fallopian tube and is accessing the outside of a fallopian tube, and a second treatment device has been advanced through the cervix and a fallopian tube and is accessing the outside of the uterus proximate a fibroid.

Referring now to FIG. 6, a preferred embodiment of a trans-fallopian method for performing a gynecologic procedure is illustrated. A first treatment device 500c is inserted through the vaginal canal of the vagina V, through the cervix C, through the uterus U and through a fallopian tube FT1 to a location outside the fallopian tube FT1. First treatment device 500c includes an elongate shaft, shaft 501c which includes on its distal end occluding assembly 510c, shown as a snaring assembly but alternatively an occluding clip placement assembly or an occlusive drug delivery assembly. Shaft 501c preferably includes one or more pull wires, for manipulation, and alternatively or additionally may be advancable over a previously placed guidewire. Shaft 501c preferably includes a handle on its proximal end, not shown but preferably including one or more controls such as pull wire controls and a control to synch up the snare of treatment element 510c. Treatment element 510c is shown having snared a portion of fallopian tube FT1 such as to occlude fallopian tube FT1 in a sterilization procedure.

A second treatment device 500d is inserted through the vaginal canal of the vagina V, through the cervix C, through the uterus U and through a fallopian tube FT2 to a location outside the fallopian tube FT2 and proximate subserosal fibroid F. In an alternative embodiment, the introducer of the present invention is placed into the cervix C, and first treatment device 500c and/or second treatment device 500d are passed into the uterus U via the introducer. In another alternative embodiment, one or more of the previous devices resides outside of the introducer, such as to stabilize that device in the uterus. Second treatment device 500d includes an elongate shaft, shaft 501d which includes on its distal end treatment element 510d, a fibroid treating element such as a morcellator, an ablative element, a lysing or excising element, or another device used to remove or denature fibroid tissue. Shaft 501d preferably includes one or more pull wires, for manipulation, and alternatively or additionally may be advancable over a previously placed guidewire. Shaft 501d preferably includes a handle on its proximal end, not shown but preferably including one or more controls such as pull wire controls and a control to activate fibroid treating element 510d.

Treatment catheter 500c and/or treatment catheter 500d may include one or more functional elements as has been described in detail hereabove. Preferably, a navigation and/or visualization element is employed to introduce the ends of the devices, especially to the target location once exiting the fallopian tube. Preferably treatment catheter 500c and/or treatment catheter 500d include one or more visualization markers, such as visible and non-visible markers; radiopaque markers; magnetic markers; ultrasonically reflective markers; and combinations thereof. Similar to the trans-vaginal-wall methods of FIGS. 5 and 5A, the trans-fallopian tube approach of FIG. 6 may be used to perform numerous procedures including but not limited to: uteral wall procedures (e.g. the fibroid F treatment shown); fallopian tube procedures (e.g. the tubal ligation shown); ovary procedures (e.g. egg harvesting); cancer treatment procedures; pain treatment procedures; other tissue treatment or removal procedures, and intra-abdominal procedures.

Figure 7:
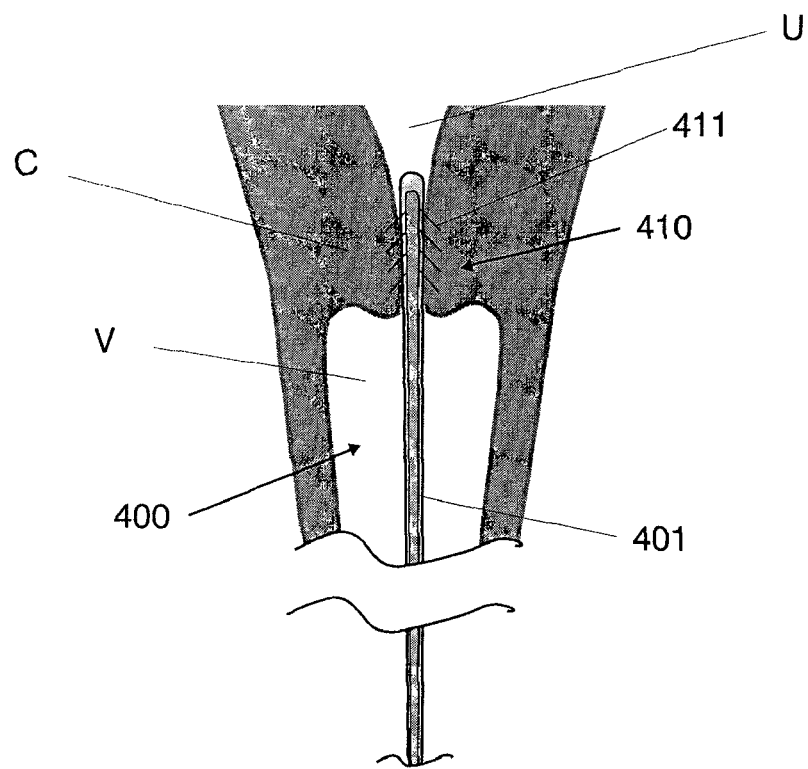
FIG. 7 illustrates a side sectional view of an exemplary drug delivery device consistent with the present invention, wherein the device is deployed in the cervix of the patient and integral needles are deployed into the cervical wall.

Referring now to FIG. 7, a preferred embodiment of a drug delivery device of the present invention is illustrated. Drug delivery device 400 is shown having been inserted into through the vagina V and into the cervix C of a patient. Device 400 includes an elongate shaft 401 with, near its distal end, drug delivery assembly 410. Drug delivery assembly 410 includes needles 411 (e.g. Nitinol or stainless steel needles), shown deployed into the cervix C such as to deliver a drug to the cervix. Applicable drugs include anesthetics such as lidocaine, muscle relaxing drugs, and other drugs. Shaft 401 may include one or more lumens, such as a fluid delivery lumen to deliver a drug to needles 411 and a guidewire lumen for preferably advancing shaft 401 into the cervix C over a guidewire.

Figure 7A:
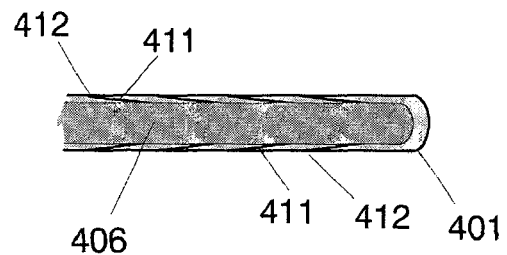
FIG. 7A illustrates a side sectional view of the drug delivery device of FIG. 7, wherein the needles are in the retracted position.
Figure 7B:
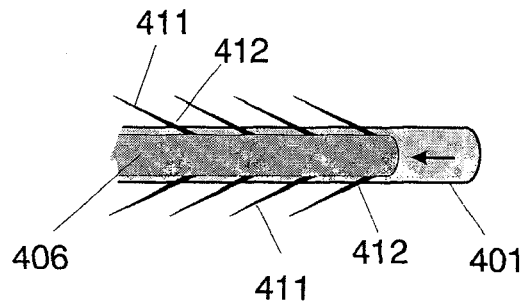
FIG. 7B illustrates a side sectional view of the drug delivery device of FIG. 7, wherein the needles are in an deployed position.
Figure 7C:
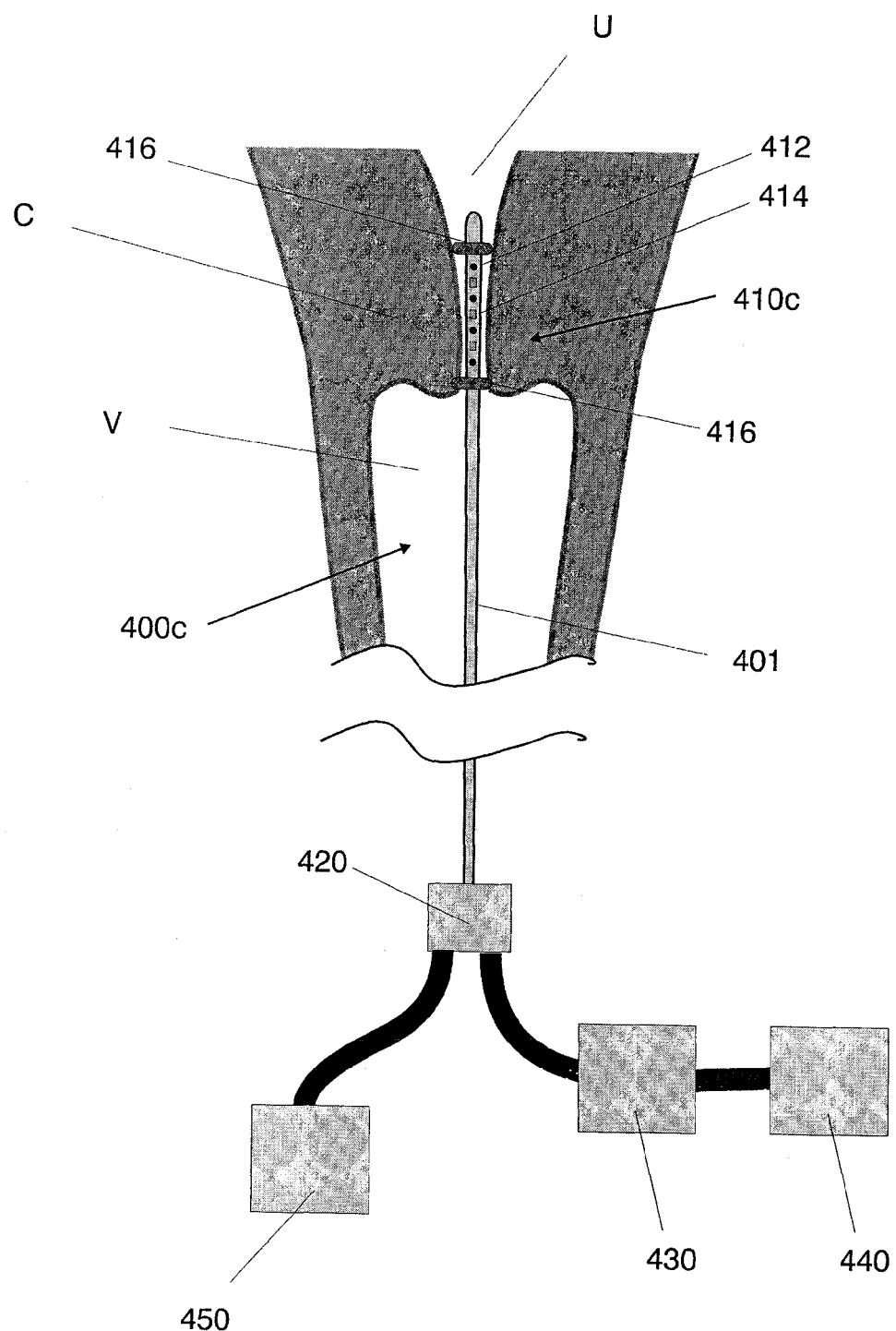
FIG. 7C illustrates a side sectional view of another exemplary drug delivery device consistent with the present invention, wherein the device includes a vacuum source and suction ports for attracting tissue toward a drug delivery element.

Referring now to FIG. 7A, the distal end of shaft 401 is shown. Shaft 401 surrounds inner shaft 406, which can be controllable advanced and retracted by the clinician such as via one or more controls on a proximal handle of drug delivery device 400, handle and controls not shown. Needles 411 are undeployed, contained within the wall of shaft 401 with their distal tips oriented toward and proximate to exit holes 412. Referring now to FIG. 7B, inner shaft 406 has been retracted, causing needles 411 to deploy, passing through exit holes 412. Such retraction would cause needles 411 to penetrate into neighboring tissue, such as cervical tissue when shaft 401 is placed in the cervix when inner shaft 406 is retracted. In order to support the intended motion, needles 411 may be flexible or may be connected to a flexible hinge.

Referring now to FIG. 7D, a preferred embodiment of a drug delivery device of the present invention is illustrated. Drug delivery device 400c is shown having been inserted into through the vagina V and into the cervix C of a patient. Device 400c includes an elongate shaft 401 with, near its distal end, drug delivery assembly 410d. Shaft 401 includes occluding rings 416 on either end of drug delivery assembly 410c. Occluding rings 416 and drug delivery assembly 410c have been positioned in the cervix C such that drug delivered through one or more exit holes 412 of drug delivery assembly 410c will contact cervical tissue. Applicable drugs include anesthetics such as lidocaine, muscle relaxing drugs, and other drugs.

Occluding rings 416 are sized to form a seal in the cervix, such as to allow elevated pressure delivery of drugs and/or to provide a vacuum seal in the area surrounding drug delivery element 410c. In an alternative embodiment, shaft 401 includes a single occluding ring 201, such as at a location of the proximal occlusion ring shown. In another alternative embodiment, occluding rings 201 may have a controllable diameter, such as rings comprising an inflatable balloon, balloon inflation lumen and inflation port not shown.

Drug delivery element 410c further includes one or more suction ports 414. Suction ports 414 and occluding rings 416 are configured such that when a vacuum is applied to suction ports 414, the cervical (or other neighboring) tissue is pulled toward the exit holes 412 of drug delivery element 410c, such that the efficacy of drug delivered through exit holes 412 is enhanced. Exit holes 412 and suction ports 414 are connected to independent hollow conduits that travel from drug delivery element 410c to port 420 on the proximal end of drug delivery device 400c. Port 420 fluidly connects to drug reservoir 430, which in turn is pressurized by pressure reservoir 440 (such as a $CO_2$ pressure source) such that fluid can flow through shaft 401 to exit holes 412. Port 420 is also fluidly connected to vacuum generator 450 such that suction can be transferred through shaft 401 (in a separate conduit than is connected to drug reservoir 430) to suction ports 414.

In an alternative embodiment, drug delivery element further includes an iontophoretic element, not shown but configured to enhance drug delivery into the tissue surrounding drug delivery element 410c. In another alternative embodiment, shaft 401 includes a lumen to support over-the-wire delivery.

Figure 8:
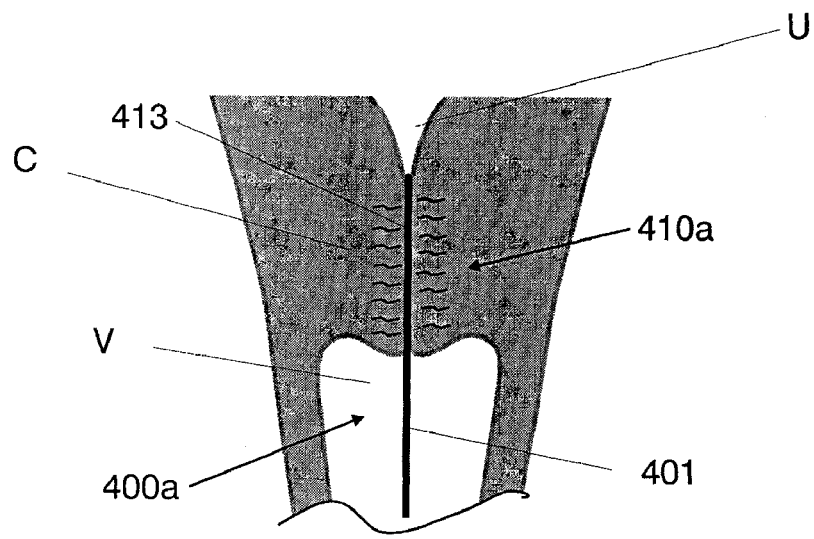
FIG. 8 illustrates a side sectional view of another exemplary drug delivery device consistent with the present invention, wherein the device is deployed in the cervix of the patient and integral exit holes allow fluid to pass into the cervical wall.

Referring now to FIG. 8, another preferred embodiment of a drug delivery device of the present invention is illustrated. Drug delivery device 400a is shown having been inserted into through the vagina V and into the cervix C of a patient. Device 400a includes an elongate shaft 401 which includes drug delivery assembly 410a near its distal end. Drug delivery assembly 410a includes exit holes needles 413, sized and configured to deliver a drug to the cervix. Applicable drugs include anesthetics such as lidocaine, muscle relaxing drugs, and other drugs. Shaft 401 may include one or more lumens, such as a fluid delivery lumen to deliver a drug to exit holes 413 and a guidewire lumen for preferably advancing shaft 401 into the cervix C over a guidewire.

Figure 8A:
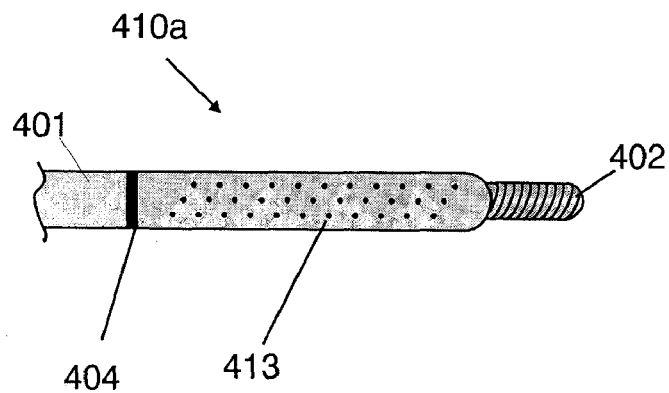
FIG. 8A illustrates a side view of the distal end of the drug delivery device of FIG. 8, wherein the device is deployed over an occluding guidewire.
Figure 8B:
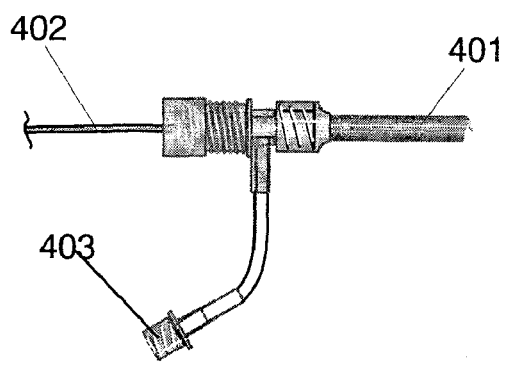
FIG. 8B illustrates a side view of the proximal end of the drug delivery device of FIG. 8A.

Referring now to FIG. 8A, the distal end of shaft 401 is shown. Shaft 401 surrounds an occluding guidewire 402. Shaft 401 can be controllably advanced and retracted by the clinician over guidewire 402. Proximal to exit holes 413 is marker 404, preferably a radiopaque or ultrasonically reflective marker used to position the exit holes 413 in the cervix C. Referring now to FIG. 8B, the proximal end of inner shaft 406 is shown wherein guidewire 402 exits the proximal end of the device. Infusion port 403 provides fluid access to the exit holes 413 such that drugs can be delivered via a syringe, infusion pump, or gravity feed system.

Figure 9:
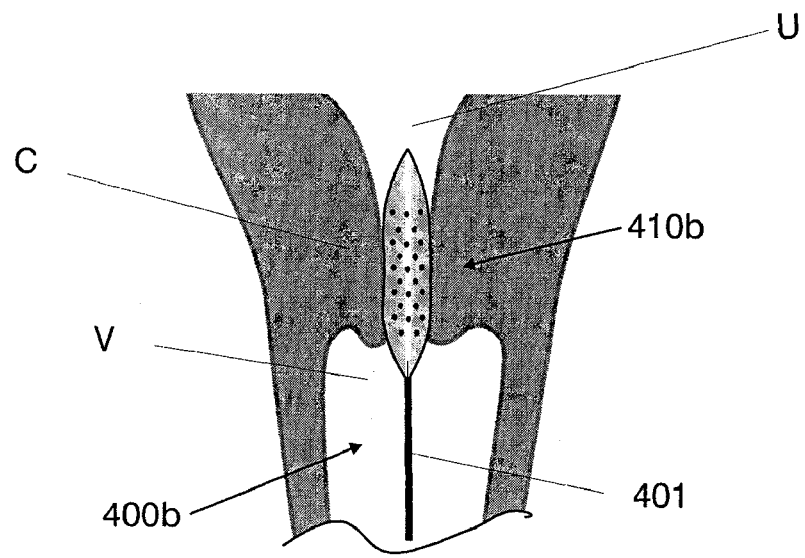
FIG. 9 illustrates a side sectional view of another exemplary drug delivery device consistent with the present invention, wherein the device is deployed in the cervix of the patient, an integral balloon has been inflated and integral exit holes in the balloon allow fluid to pass into the cervical wall.

Referring now to FIG. 9, another preferred embodiment of a drug delivery device of the present invention is illustrated. Drug delivery device 400b is shown having been inserted into through the vagina V and into the cervix C of a patient. Device 400a includes an elongate shaft 401 with, near its distal end, drug delivery assembly 410b comprising a balloon with multiple exit holes which are sized and configured to deliver a drug to the cervix. Applicable drugs include anesthetics such as lidocaine, muscle relaxing drugs, and other drugs. Shaft 401 may include one or more lumens, such as a fluid delivery lumen to deliver a drug to exit holes 413 and a guidewire lumen for preferably advancing shaft 401 into the cervix C over a guidewire.

Figure 9A:
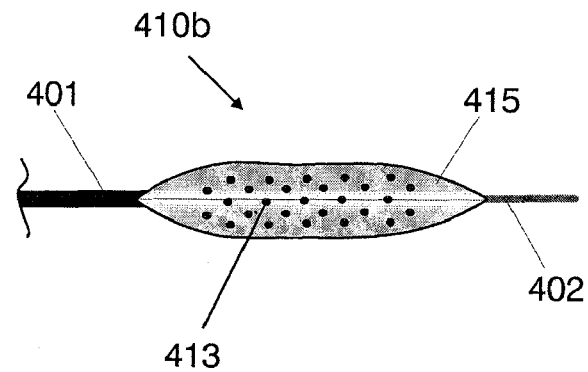
FIG. 9A illustrates a side view of the distal end of the drug delivery device of FIG. 9, wherein the device is deployed over a guidewire and the balloon is inflated.
Figure 9B:
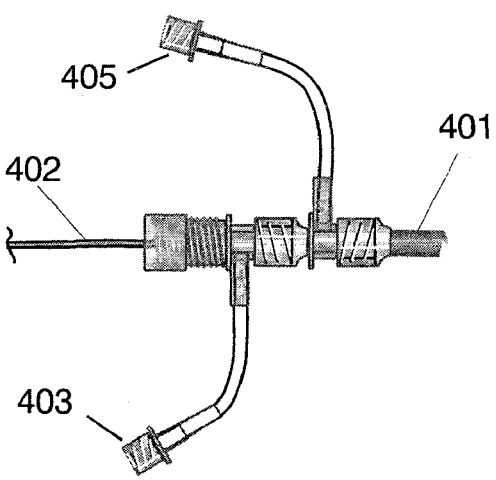
FIG. 9B illustrates a side view of the proximal end of the drug delivery device of FIG. 9A.

Referring now to FIG. 9A, the distal end of shaft 401 is shown having been inserted over guidewire 402. Shaft 401 can be controllably advanced and retracted by the clinician over guidewire 402. Drug delivery assembly 410b includes an inflatable balloon 415, preferably a dual balloon construction with exit holes 413 in the outer balloon. Referring now to FIG. 9B, the proximal end of inner shaft 406 is shown wherein guidewire 402 exits the proximal end of the device. Infusion port 403 provides fluid access to the exit holes 413 such that drugs can be delivered via a syringe, infusion pump, or gravity feed system. Inflation port 406 provides inflation access to balloon 415, such as to an inner balloon portion of balloon 415. In an alternative embodiment, an enhanced drug delivery element is integral to balloon 415, such as an iontophoretic element for precision controlled drug delivery. In another alternative or additional embodiment, balloon 415 is inflated to dilate or partially dilate the cervix C of the patient.

Figure 10:
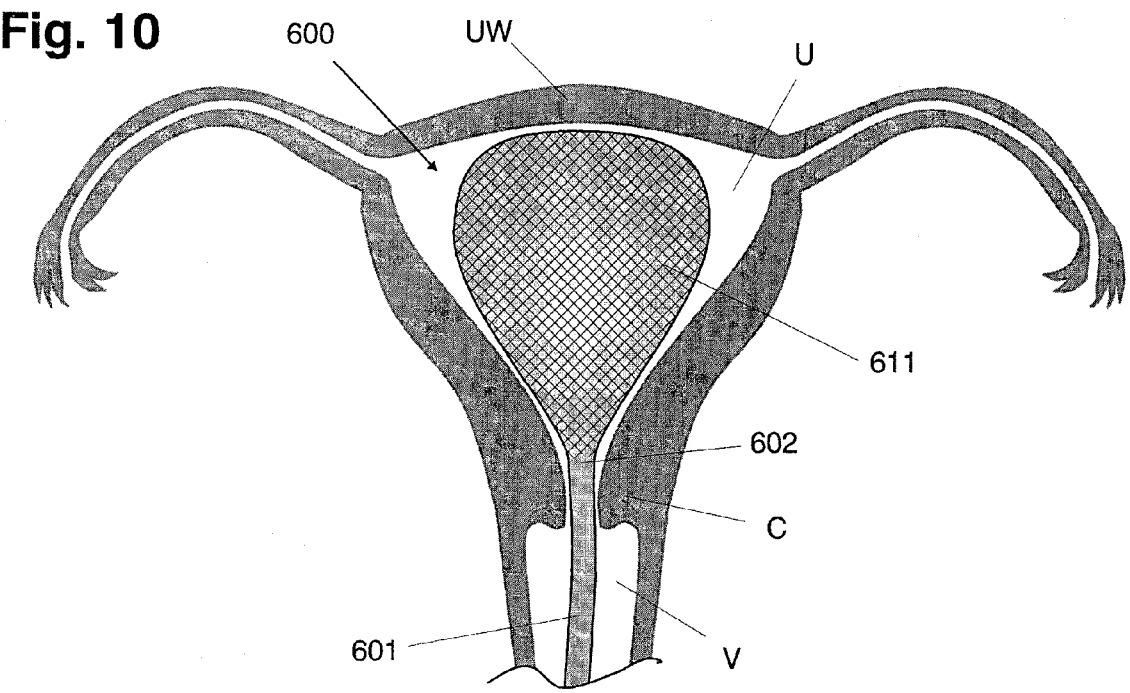
FIG. 10 illustrates a side sectional view of an exemplary scaffolding device consistent with the present invention, wherein the device has been deployed in the uterus of a patient.

Referring now to FIG. 10, a preferred embodiment of a scaffolding device of the present invention is illustrated. Scaffolding device 600, and the other distension devices of the present invention, are preferably inserted into the uterus of a patient such that the scaffolding assembly preferably distends the uteral cavity to a volume equivalent to that which would be attained via a liquid distension media at a pressure of at least 40 mm of HG but not greater than 100 mm HG and preferably approximating 70 mm Hg. Scaffolding device 600 is shown having been inserted into through the vagina V, through the Cervix C and into the uterus U of a patient. In an alternative embodiment, the introducer of the present invention is placed into the cervix C, and scaffolding device 600 is passed into the uterus U via the introducer. Scaffolding device 600 includes elongate shaft 601. Extending beyond the distal tip 602 of shaft 601 is deployable basket 611. Basket 611, shown in its fully expanded state, is preferably a resiliently biased foldable weave of filaments made of Nitinol. Manipulation of shaft 601 (e.g. via pull-wires not shown) and/or basket 611 can be performed by the clinician to exert forces against one or more portions of the uteral wall UW such as to distend or scaffold the uteral wall, to apply tamponade to a bleed, and combinations thereof. Basket 611 can be arranged in numerous shapes, such as to mimic the shape of the uterus or a portion of the uterus. The weaved filaments may be sized (e.g. diameter, length or width) to effectively cover a small proportional area (e.g. large "windows" between filaments) or they may be configured to cover a large proportion of the area (e.g. with a large profile and/or a covering).

Basket 611 may include a covering, on the inside or the outside of the resiliently biased structure, and the covering may be a partial covering. In a preferred embodiment, a clinician places a tamponade force on a bleeding tissue location with a covered portion of basket 611. In another preferred embodiment, a clinician reduces the amount of fluid used in a procedure by inserting a scaffolding device 600 that includes a covering of basket 611 (i.e. the basket occupies space in the uterus and/or limits fluid transfer from the portion of the uteral wall in contact with the balloon). Basket 611 and any associated coverings may be coated, impregnated or otherwise include one or more drugs, such as clotting agents and anesthetics. In a preferred embodiment, the drug may be "released" by the clinician on demand, such as by an integral iontophoretic delivery element (e.g. integral to basket 611), or by applying a force to an integral pressure activated drug depot (e.g. integral to basket 611). Basket 611 and any associated coverings may be coated or treated with one or more compounds to change a property such as lubricity and radiopacity. Avoiding or reducing the need for distension with fluid subsequently reduces the risk factors (e.g. intravasation) associated with that fluid delivery.

Figure 10A:
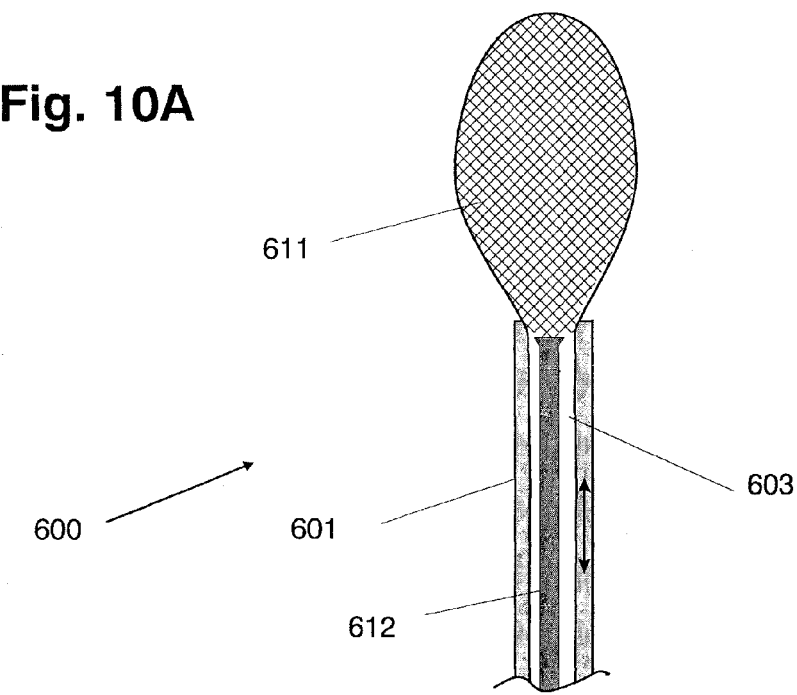
FIG. 10A illustrates a side sectional view of the scaffolding device of FIG. 10, wherein a control shaft has been near fully extended and a scaffold is partially deployed.

Referring now to FIG. 10A, a cross section of the distal portion of scaffolding device 600 is shown with basket 611 in a near-fully deployed state. Basket 611 is fixedly attached to control shaft 612 which is slidingly received by outer shaft 601 via lumen 603. The proximal end of shaft 601 is preferably attached to a handle, not shown, which includes one or more controls, also not shown but preferably including a control knob or lever that can precisely advance and retract control shaft 612. Retraction of control shaft 612 causes basket 611 to withdraw into the lumen 603 of shaft 601 and transition to a radially compact state. Subsequent advancement of control shaft 612 causes bases 611 to exit lumen 603 and resiliently expand into the deployed state shown if FIG. 10. In an alternative embodiment, basket 611 includes mechanical expansion means to assist in radial expansion, such mechanical expansion means including an inflatable balloon inside or outside of basket 611, advancable push rods which exert radial forces upon different portions of basket 611 and/or other mechanical means. In this alternative embodiment, basket 611 may or may not be resiliently biased.

In a preferred embodiment, basket 611 can be expanded in the uterus (or other body cavity), and a procedure such as a tissue removal or denaturing procedure be performed "through" the weave of basket 611. Numerous one or more treatment or other devices, can be used by the clinician while scaffolding device 600 is in place in the uterus. In particular, tissue treatment devices (e.g. morcellators; radiofrequency, laser and cryogenic ablaters; and subsonic treatment devices) and drug delivery devices can perform their intended function, such as to treat tissue present in between the filaments (tissue in "window) of basket 611. In another preferred embodiment, scaffolding device 600 is used to treat uteral prolapse. In yet another preferred embodiment, a separate balloon catheter is inserted within balloon 611, such as to occupy space and/or apply additional force to the uteral wall. In yet another alternative embodiment, one or more portions of basket 611 can be energized (e.g. deliver RF energy to tissue) in order to treat tissue, which may avoid the need for a second device.

Figure 10B:
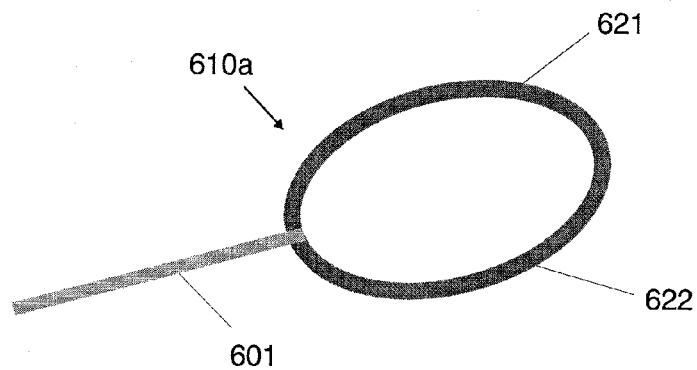
FIG. 10B illustrates a perspective view of an exemplary scaffolding device consistent with the present invention, wherein the scaffolding assembly comprises two resiliently biased arms.

Referring now to FIG. 10B, another preferred embodiment of a scaffolding device of the present invention is illustrated. Located on the distal end of elongate shaft 601 is a deployable scaffolding assembly 610a. Scaffolding assembly 610a is configured to scaffold open a body cavity such as the uterus, while also providing an operating space to perform one or more procedures such as tissue removal. Scaffolding assembly 610a make be arranged in one or more shapes, such as to conform to specific body areas such as the contour of uteral wall. Scaffolding assembly 610a comprises two resiliently biased arms, first arm 621 and second arm 622. These arms, preferably constructed of Nitinol, are configured to be radially compressed when drawn into the distal end of a tube, such as the lumen of the introducer of the present invention (see FIG. 10D). Shaft 601 preferably includes one or more lumens, such as a lumen to slidingly receive a guidewire for over-the-wire delivery. In an alternative embodiment, first arm 621 and/or second arm 622 include light source means, such as light provided through a window optically connected to a fiber optic cable, light provided by one or more LEDs and/or light provided via a chemoluminescent solution.

Figure 10C:
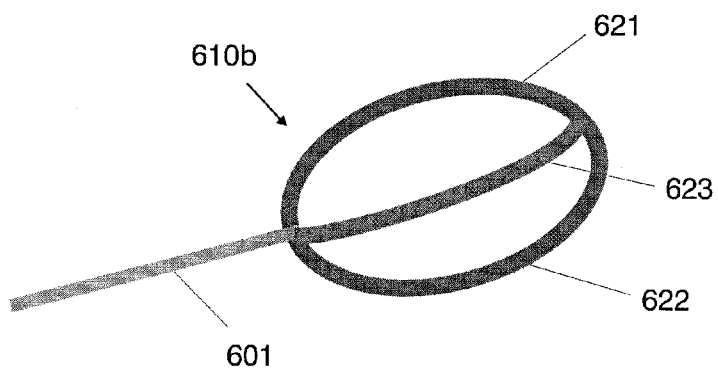
FIG. 10C illustrates a perspective view of an exemplary scaffolding device consistent with the present invention, wherein the scaffolding assembly includes three resiliently biased arms.

Referring now to FIG. 10C, another preferred embodiment of a scaffolding device of the present invention is illustrated. Located on the distal end of elongate shaft 601 is a deployable scaffolding assembly 610b. Scaffolding assembly 610b (similar to is configured to scaffold open a body cavity such as the uterus, while also providing an operating space to perform one or more procedures such as tissue removal. Scaffolding assembly 610b make be arranged in one or more shapes, such as to conform to specific body areas such as the contour of uteral wall. Scaffolding assembly 610b comprises three resiliently biased arms, first arm 621, second arm 622 and third arm 623. In an alternative embodiment, four or more arms may be included. These arms, preferably constructed of Nitinol, are configured to be radially compressed when drawn into the distal end of a tube, such as the lumen of the introducer of the present invention (see FIG. 10D). Shaft 601 preferably includes one or more lumens, such as a lumen to slidingly receive a guidewire for over-the-wire delivery. In an alternative embodiment, first arm 621, second arm 622 and/or third arm 623 include light source means, such as light provided through a window optically connected to a fiber optic cable, light provided by one or more LEDs and/or light provided via a chemoluminescent solution.

Figure 10D:
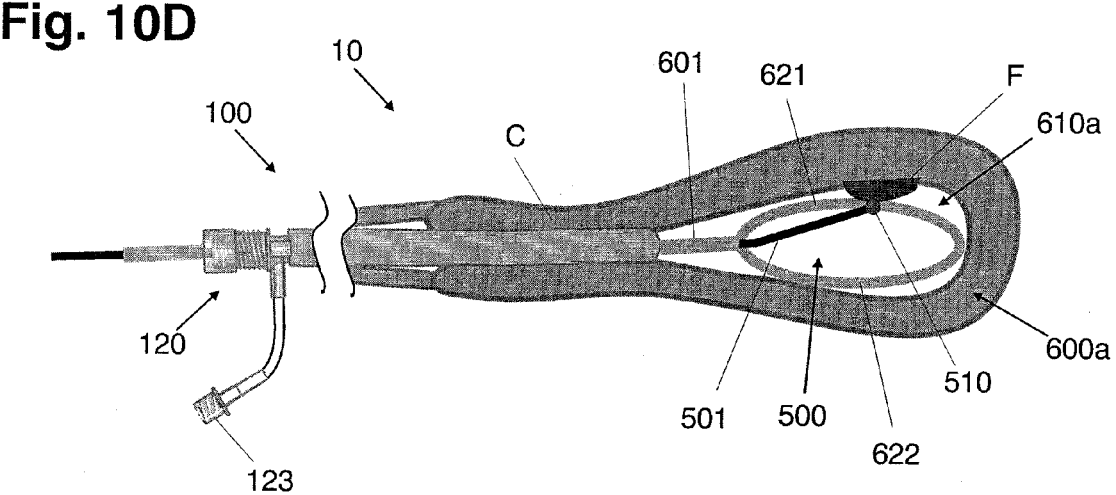
FIG. 10D illustrates a side sectional view of the scaffolding device of FIG. 10B, wherein the scaffolding device has been inserted through an introducer of the present invention and has its distal portion in the uterus of a patient.

Referring now to FIG. 10D, a preferred embodiment of a system 10 consistent with the present invention is illustrated. System 10 includes introducer 100, scaffolding device 600a and treatment device 500. Introducer 100d includes sheath 110, device insertion port 120 and fluid transfer port 123, all of similar construction to similar components of introducers 100a, 100b and 100c, 100d, 100e, 100f and 100g hereabove. Introducer 100 has been placed and advanced such that its distal portion resides within cervix C and its distal end provides access within uterus U of a patient.

Scaffolding device 600a, of similar construction to the scaffolding device of FIG. 10B, has been advanced through a lumen of introducer 100 such that the distal end of shaft 601 and scaffold assembly 610a (fully expanded) reside within the uterus U such that a scaffolding force is applied to the uteral wall along a plane relatively perpendicular to the cross section shown in FIG. 10D. First arm 621 and second arm 622 have been positioned at locations away from uteral fibroid F as shown in FIG. 10D. Treatment device 500 has been coaxially advanced through a lumen of shaft 601 of scaffolding device 600a such that the distal portion of shaft 501 resides with uterus U. At the distal end of shaft 501 is treatment element 510, such as a morcellator or other tissue treatment element. Via deflection means, not shown but preferably a pull-wire internal to shaft 501, treatment element 510 has been brought in close proximity to fibroid F, also as shown in FIG. 10D.

In an alternative embodiment, treatment catheter 500, scaffolding device 600a and/or introducer 100 include a visualization apparatus such as a camera to visualize inside uterus U, such as when clear fluid is introduced into uterus U via port 123. Light may be provided, as has been described in detail hereabove, from a functional element integral to the distal portions of treatment catheter 500 (e.g. proximate a camera which is proximate treatment element 510), scaffolding device 600a (e.g. in one or more of arms 621 and 622) and/or introducer 100 (e.g. a forward beam light source) such as to improve the image provided to the clinician via the integral camera. In one embodiment, the camera is an infrared camera and heated and/or cooled solutions are utilized to increase the contrast in the infrared image (tissue temperature differences) and reduce or eliminate the need for an external light source.

In the performance of one or more gynecologic and urologic procedures, such as a tissue removal or other treatment procedure, scaffolding device 600a and treatment device 500 are repositioned, such as to scaffold a different part of the uterus or to access a different portion of tissue, respectively. In a preferred embodiment, a second scaffolding device is inserted through introducer 100, simultaneous with or at a different time than scaffolding device 600a resides within introducer 100. In another preferred embodiment, a second treatment device is inserted through introducer 100, simultaneous with or at a different time than treatment device 500 resides within introducer 100.

Figure 11:
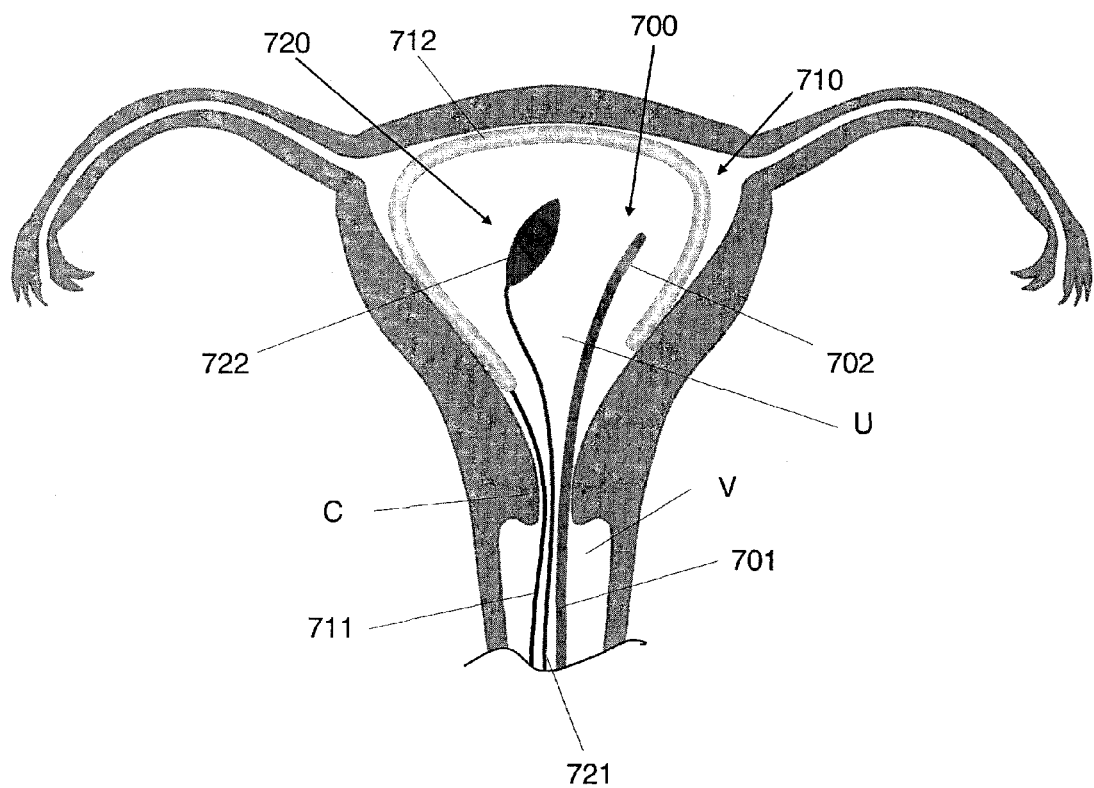
FIG. 11 illustrates a side sectional view of an exemplary visualization apparatus consistent with the present invention, wherein a camera device, a first light source and a second light source have been advanced into the uterus of a patient.

Referring now to FIG. 11, a preferred embodiment of a visualization apparatus of the present invention is illustrated. Camera device 700 consists of shaft 701, preferably an elongate shaft with a deflectable tip, which includes camera assembly 702 in its distal end portion. Camera assembly 702, which preferably includes a sealed lens or window on its outer portion, includes one or more configurations as has been described hereabove, including one or more components or assemblies selected from the group consisting of: lenses including filtering lenses, wide angle lenses, gradient lenses and focusing lenses; mirrors; image sensors such as a CCD module; MEMS gyroscopes (such as to detect and accommodate for motion); MEMS mirrors; light sources such as LEDs; strain gauges (such as to detect and accommodate for motion); accelerometers (such as to detect and accommodate for motion); fiber optic cable for image transfer; other optical or image processing components and combinations thereof. Camera assembly 702 may be arranged as an endoscope, and/or may involve different technologies such as MEMS actuators, CCD modules and motion detectors which are configured to provide a stabile image to a clinician despite camera movement. In an alternative embodiment, an output port, not shown, is located proximate to camera assembly 702 such that saline or other biocompatible liquid media in fluid communication with the output port can be flushed by camera assembly 702 such as to clear debris and improve image quality. Camera device 700 provides an image to a display, not shown but preferably a laptop screen as has been described in reference to FIG. 5, such as through an electrical and/or optical connection on a handle of camera device 700.

The visualization apparatus of FIG. 11 further includes a first light source 710 which is independent (e.g. independently maneuverable) from camera device 700. First light source 710 includes shaft 711, preferably an elongate shaft with a deflectable tip, which includes light emitting element 712 at its distal end. Light emitting element 712 is a tubular structure which can be shaped, via pull wire technology described above and/or via plastic deformation (e.g. plastically deformable wire included within light emitting element 712) such as to wrap around the uterus as shown in FIG. 11. Light emitting element 712 is preferably a self-contained light source, such as an array of light emitting diodes that are surrounded by a window such as a diffracting or light-scattering lens. In an alternative embodiment, light emitting element 712 does not include a light source, but rather consists of a viewing window in optical communication with one or more fiber optic cables which in turn connect to a light source, the light source being integral to first light source 710 (such as in a handle of the device) or external and optically connected to first light source 710. Light emitting element 712, or a separate light source that supplies light emitting element 712, is connected to a source of electrical power such as a battery (e.g. a battery in a handle of the device). In an alternative embodiment, light emitting element 712 emits light from a chemoluminescent solution (e.g. a chemoluminescent solution that is mixed on demand by the clinician, such as by one or more controls on the handle of the device). This light generating solution, as in found in commercially available "lightsticks", may be contained (sealed compartment) within light emitting element 720, or be optically connected to element 720 via a fiber optic cable. In an alternative embodiment, the chemoluminescent solution is introduced into light emitting element 720 via an infusion lumen. In another alternative embodiment, both a chemoluminescent solution and another source of light (e.g. LED light) are provided by light emitting element 720.

The visualization apparatus of FIG. 11 further includes a second light source 720 which is also independent (e.g. independently maneuverable) from camera device 700. Second light source 720 includes shaft 721, preferably an elongate shaft with a deflectable tip, which includes light emitting element 722 at its distal end. Light emitting element 722 is a balloon structure which can be inflated and deflated by the clinician, shown in the inflated or partially inflated state in FIG. 11. Light emitting element 722 is preferably a self-contained light source, such as a vessel into which chemoluminescent solution is delivered, as has been described hereabove. Alternatively, one or more light emitting diodes that are surrounded by a covering (the balloon) which is configured as a diffracting or light-scattering lens. In an alternative embodiment, light emitting element 722 does not include a light source, but rather consists of a viewing window (the balloon) in optical communication with one or more fiber optic cables which in turn connect to a light source, the light source being integral to second light source 720 (such as in a handle of the device) or external and optically connected to second light source 720. Light emitting element 722, or a separate light source that supplies light emitting element 722, may be connected to a source of electrical power such as a battery. In the preferred embodiment, light emitting element 722 emits light from a chemoluminescent solution (e.g. a chemoluminescent solution that is mixed on demand by the clinician and injected into the balloon of light emitting element 722, such as by one or more controls on the handle of the device) and does not require the source of electrical power. In an alternative embodiment, both a chemoluminescent solution and another source of light (e.g. LED light) are provided by light emitting element 722.

Camera device 700, first light source 710 and second light source 720 have had their distal ends placed through the cervix C and into the uterus C of a patient. In an alternative embodiment, the introducer of the present invention is placed into the cervix C, and camera device 700, first light source 710 and/or second light source 720 are passed into the uterus U via the introducer. In another alternative embodiment, one or more of the previous devices resides outside of the introducer, such as to stabilize that device in the uterus. Each device preferably includes a handle on their proximal end, not shown but preferably including one or more controls including but not limited to: knobs or levers to manipulate one or more pull wires configured to manipulate the distal portions of the associated device; a control to zoom in or zoom out an image; a control to focus an image; a control to stabilize an image; a control to energize a light source; a control to change the light intensity of a light source (e.g. via change to energy supplied); a control to deliver a drug; a control to change the speed of a tissue removal assembly; a "Kill-switch" control to stop motion of a component immediately; other controls and combinations thereof.

In addition to the above controls, each handle may include one or more ports, such as ports selected from the group consisting of: a valved port such as a cracking pressure valved port, a two-way valved port and a duckbill valved port; a Tuohy-Borst valve; a fluid stasis valve; a device insertion port such as a port configured to accept a treatment device of the present invention; an infusion lumen access port such as an infusion lumen in fluid communication with a drug reservoir, exit port or other component of a drug delivery element; a balloon inflation lumen access port; other ports and combinations thereof. In a preferred embodiment, camera device 700, first light source 710 and/or second light source 720 include one or more integral functional elements such as a drug delivery element or other functional element as have been described hereabove. In a preferred embodiment, the functional element is an integral inflatable balloon, not shown but preferably in a distal portion of the device and configured to: occupy space in the uterus, deflect the distal end of the associated device by applying a force to the uteral wall; apply tamponade force to the uteral wall, or distend the uterus.

The distal portions of camera device 700, first light source 710 and second light source 720 may be manipulated in the uterus U such as to perform a secondary function including but not limited to: applying a tamponade force to a portion of the uteral wall (e.g. a perforation or bleed); to distend the uterus; and combinations thereof. The distal portions of camera device 700, first light source 710 and second light source 720 have an "effective" outer diameter (e.g. the ID of an appropriate sheath 110 of the present invention) less than 9 mm, preferably between 5 and 8 mm, and more preferably less than 6 mm.

Figure 12:
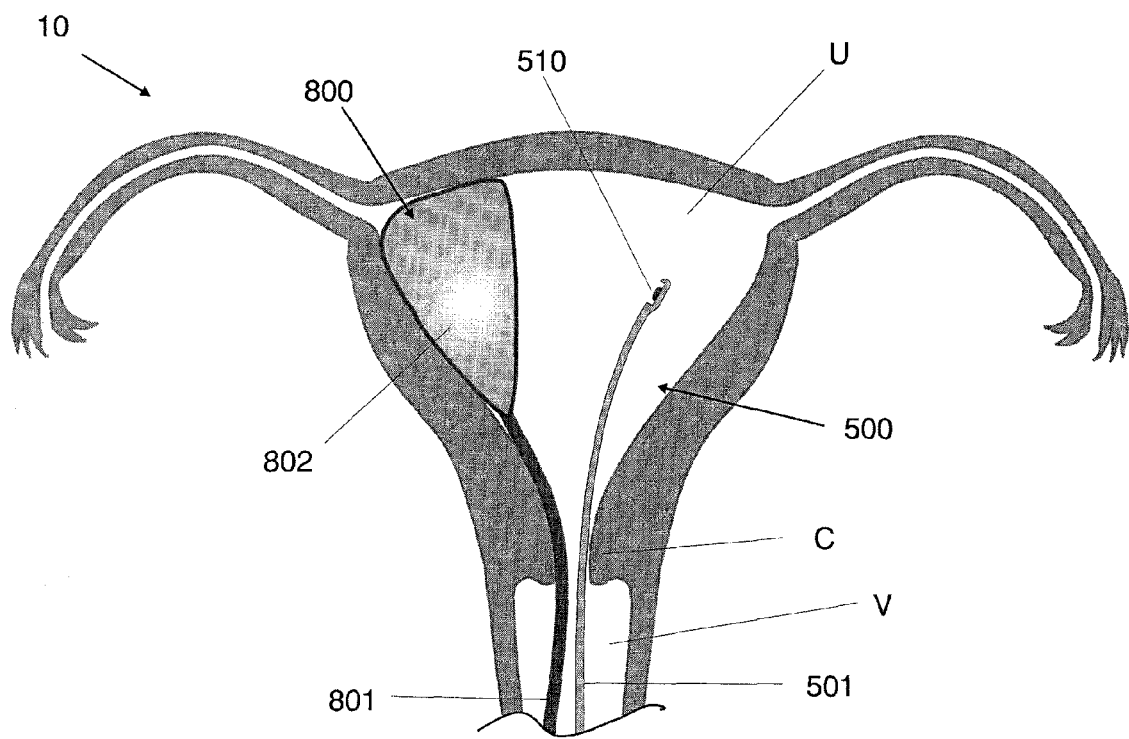
FIG. 12 illustrates a side sectional view of another exemplary system consistent with the present invention, wherein a uteral volume occupying device and a treatment device have each been advanced into the uterus of a patient.

Referring now to FIG. 12, a preferred embodiment of a volume occupying device of the present invention is illustrated. Volume occupying device 800 consists of shaft 801, preferably an elongate shaft with a deflectable tip, which includes volume occupying balloon 802 in its distal end portion. Inflation of balloon 802 is accomplished by administering fluid such as saline from an inflation port, not shown but preferably on a handle on the proximal end of device 800. Balloon 802 may be a compliant balloon such expands to variable volumes based on the fluid pressure, or a non-compliant balloon configured to expand to a fixed volume, relatively independent of fluid pressure. Balloon 802 is preferable includes nylon and/or PET materials. Balloon 802 is configured to assume a shape when inflated that approximated the shape of the uterus or a portion of the space of the uterus, as shown in FIG. 12. Inflation of balloon 802 is performed to accomplish one or more of the following functions: distend uterus U; effectively "cover" a portion of tissue surface area of uterus U such that fluids internal to uterus U will not be absorbed by or otherwise pass through that covered portion of tissue; apply a tamponade force to a portion of the uteral wall (e.g. a bleed or puncture site); occupy space of the uterus to reduce injected fluid volume; and other functions. In a preferred embodiment, device 800 performs at least two functions listed immediately hereabove. In another preferred embodiment, device 800 performs the function of distending tissue (e.g. the uteral wall) as well as limiting the transfer of fluids into or through that tissue.

Also shown in FIG. 12 is treatment catheter 500, including an elongate shaft 501 and a treatment element 510 near the distal end of shaft 501. Treatment catheter 500, for example a tissue removal or denaturing device or a drug delivery device, is being advanced such as to a location to the right and above balloon 802 of volume occupying device 800. Advantages of placement of volume occupying device 800 include the functions in the paragraph above, as well as creating a small "work area" for the clinician to navigate with treatment catheter 500.

In an alternative embodiment, the introducer of the present invention is placed into the cervix C, and volume occupying device 800 and/or treatment catheter 400 are passed into the uterus U via the introducer. In another alternative embodiment, one or more of the previous devices resides outside of the introducer, such as to stabilize that device in the uterus.

Figure 12A:
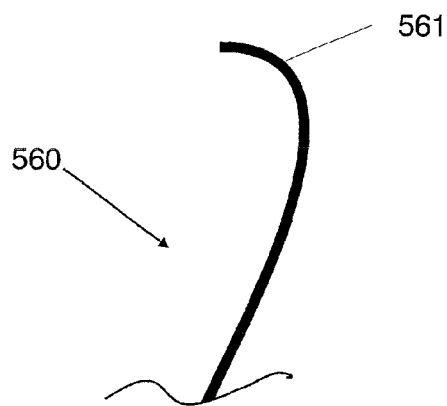
FIG. 12A illustrates a side view of an exemplary wire shaping device consistent with the present invention.

Referring additionally to FIG. 12A, a shaping wire 560 including shape 561 near its distal end is shown. Shaping wire 560, preferably a heat-set shaped Nitinol wire, is configured to be inserted into a lumen of a device, such as a lumen of volume occupying device 800 or treatment catheter 500, lumens not shown. Clinician insertion of shaping wire 560 causes the distal portion of the device in which wire 560 is inserted, to change shape in a pre-determined manner. This shape-changing function allows the clinician to position one or more components of the devices (e.g. balloon 802 or treatment element 510), at a specific location within uterus U. In a preferred embodiment, shaping wire 560 is configured to be inserted into a lumen of one or more of the introducers, treatment catheters, distension devices, volume occupying devices, visualization apparatus, navigating apparatus or other devices of the present invention such as to modify the shape of a distal portion of the device.

Figure 13:
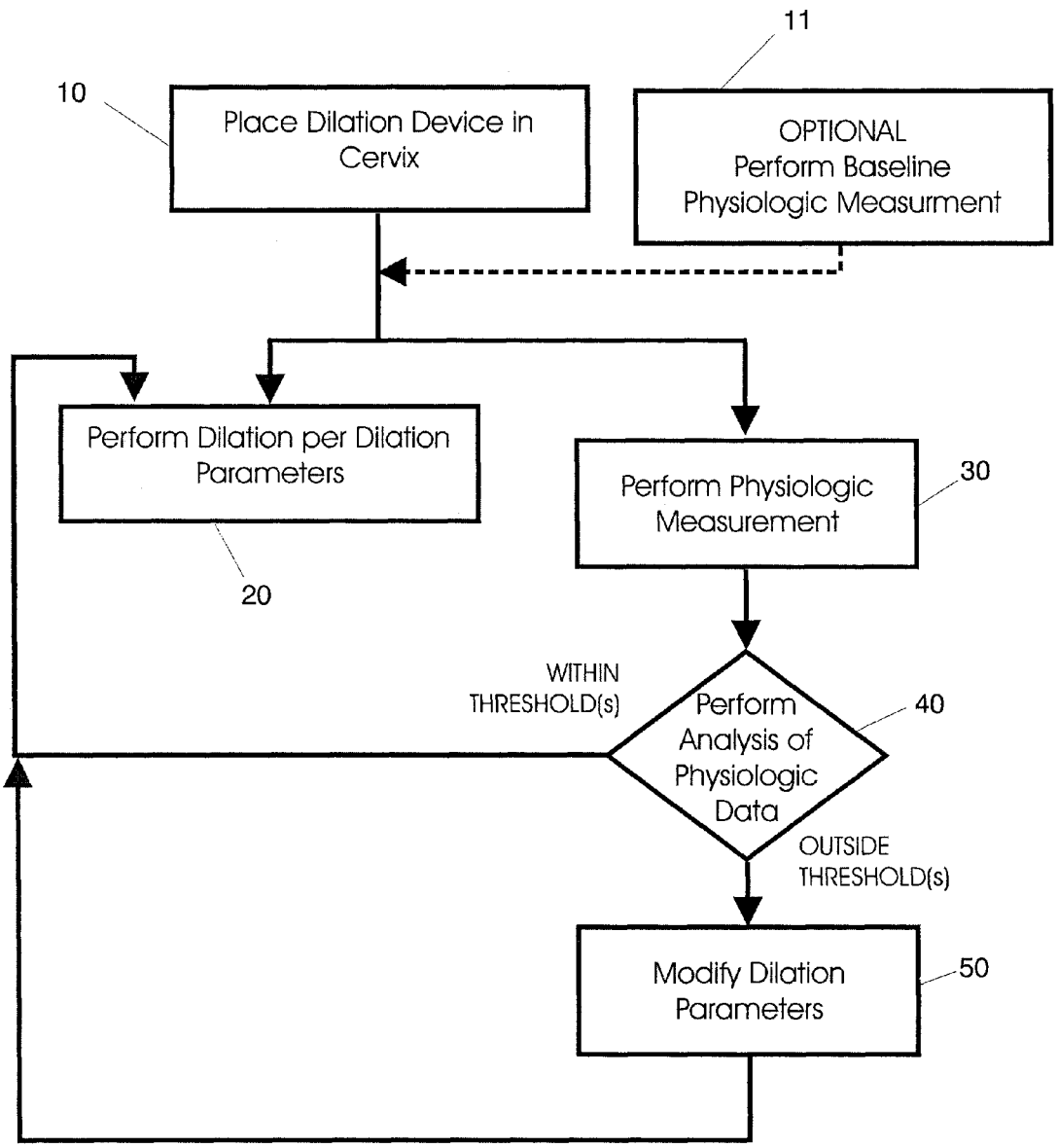
FIG. 13 illustrates a flow chart of an exemplary method of dilation, consistent with the present invention.

Referring now to FIG. 13, a preferred method and associated system of the present invention is disclosed. Numerous procedural steps listed below in reference to FIG. 13 have been described in detail throughout this specification. For brevity, the details of each step will not be repeated below but should be considered within the scope of the method and system of FIG. 13 as has been described hereabove.

Step 10 involves placing one or more devices to dilate the cervix of a patient. Prior to, during and/or shortly after the dilation of Step 10, Step 11 may be performed which is the measurement of one or more patient parameters, such as patient physiologic parameters. Patient physiologic parameters include but are not limited to: force exerted by or on tissue such as force exerted by or on the cervix as measured by a transducer integral to a cervical dilator; EKG; EEG; blood and blood gas parameters such as cell counts and $O_2$ saturation levels; glucose parameters; pH; blood pressure; respiration; and combinations thereof.

Subsequent to Step 10, Step 20 involves the dilation of the patient's cervix. The dilation is performed per a set of dilation parameters, such parameters including but not limited to: pressure of dilation such as balloon pressure; amount of dilation per unit time; pressure increase per unit time; rate of change of dilation per unit time; rate of change of pressure increase per unit time; duty cycle of discontinuous dilation (e.g. on and off times if dilation performed in discrete time segments); frequency of discontinuous dilation; other dilation parameters and combinations thereof.

Simultaneous with the performance of the dilation of Step 20, Step 30 is performed in which one or more patient parameters, as have been listed above in reference to Step 11, are taken. Step 40 is performed, in which the one or more parameters are analyzed and the results of the analysis is compared to a threshold. If a threshold is exceeded, that information is fed to the parameter modifying algorithm of Step 50, which in turn modifies one or more of the dilation of parameters of Step 20 (such as to decrease dilation pressure or stop dilation entirely). If the threshold is not exceeded, that information is fed back to the dilation control of Step 20 and no change is made.

For example, if one of the patient parameters collected in Step 30 is blood pressure, which may be an acceptable surrogate for pain level, when a previously determined blood pressure threshold is reached, dilation is reduced or stopped. The parameter analysis may be more sophisticated that comparing the physiologic measurement to a direct threshold, other analysis made additionally or alternatively be performed such as to look at rate of change of the parameter, or to analyze two or more parameters in combination: such as two or more of EKG, blood pressure and respiration.

In a preferred embodiment, a system is provided to automatically perform the parameter analysis of Step 40 and automatically modify the dilation parameters of Steps 50 and 20. In an alternative embodiment, the clinician may perform one or more steps, or perform a portion of one or more steps manually. In another preferred embodiment, one or more thresholds involved with the analysis are programmable by the clinician. In another preferred embodiment, the mathematical formulas of the analysis are programmable by the clinician.

The dilation performed in Step 20 may be accomplished with continuous application of pressure or discontinuously in discrete time segments. These discrete dilation time segments may be fractions of seconds, multiple seconds or even minutes. In a preferred embodiment, the analysis of the physiologic measurement is performed between dilation time segments, such that the subsequent dilation time segment is potentially modified (Step 50) due to the analysis performed in the previous "off" or no-dilation period.

The "smart" dilation system and method of FIG. 13 is preferably accomplished using an introducer of the present invention, such as introducer 100c of FIG. 1B which includes strain gauge 113 (output of strain gauge 113 is the measured physiologic parameter); or introducer 100e of FIG. 4 which includes pressure sensor 154 integral to dilating balloon 116 (output of sensor 154 is the measured physiologic parameter). Other devices of the present invention may include a functional element such as a pressure or other force sensor which provides an output signal that includes the physiologic data analyzed in Step 40.

In an alternative embodiment, the "smart" dilation system and method of FIG. 13 may deliver a drug based on the physiologic data analysis of Step 40, in addition to or alternative to modifying the dilation parameters in Step 50. In a preferred embodiment, a threshold for one analysis (based on one or more physiologic data) causes a drug to be delivered, and the threshold for a second analysis (based on similar or dissimilar physiologic data analysis used in the first analysis) causes a dilation parameter to be changed (including cessation of dilation).

It should be understood that numerous other configurations of the systems, devices and methods described herein could be employed without departing from the spirit or scope of this application. While the procedures described above have been described in terms of gynecological procedures, other applicable procedures can be incorporated without departing from the spirit and scope of the invention, particularly procedures applicable to both male and female patients.

The scaffolds and volume occupying element of the present invention comprise shapes and sizes that preferably allow both visualization (such as via an internal camera) and treatment (the performance of the intended clinical procedures, such as a tissue treatment procedure). Preferred shapes of these devices include but are not limited to: spherical; conical; trapezoidal; hemispherical; scallop-shaped; and combinations of the above such as a scaffolding device with a spherical portion and a conical portion. The size of the volume occupying elements of the present invention should be more than 5% of the volume of the cavity into which it is inserted (e.g. the uterus) and up to 100% of that space (e.g. to allow maximum viewing and working area without damaging tissue such as uteral wall or neighboring tissue).

The devices of the present invention may be provide in kits, such as kits that offer various size and shape scaffolding and volume occupying devices.

Each device (e.g. treatment device) could be used in various areas—not just Uterus Each device (e.g. treatment device) could be used in various procedure types such as: percutaneous, laparoscopic, MIS, open surgery Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A method of preventing intravasation during an intrauterine procedure, comprising the steps of:
   transcervically accessing the uterus with an elongate tubular sheath;
   introducing a mechanical distension device through the sheath and into the uterus, while the mechanical distension device is in a retracted state;
   distending the uterus by expanding the mechanical distension device from the retracted state into an expanded state so as to distend the uterus and expose a site;
   introducing a surgical device while the mechanical distension device remains within the uterus in the expanded state; and
   performing a surgical procedure at the site with the surgical device and with the mechanical distension device in the expanded state within the uterus,
   wherein the mechanical distension device comprises an inflatable device, wherein the step of introducing the mechanical distension device into the uterus while the mechanical distension device is in a refracted state comprises introducing the mechanical distension device into the uterus with the inflatable device in a deflated state.

2. A method of preventing intravasation during an intrauterine procedure as in claim 1, wherein the transcervically accessing step comprises advancing the sheath over a guidewire.

3. A method of preventing intravasation during an intrauterine procedure as in claim 1, wherein the transcervically accessing step is accomplished under local anesthesia.

4. A method of preventing intravasation during an intrauterine procedure as in claim 1, wherein the distending step achieves an equivalent distension to that achieved by introduction of a liquid distension media at a pressure of at least 40 mm Hg.

5. A method of preventing intravasation during an intrauterine procedure as in claim 1, wherein the distending step achieves an equivalent distension to that achieved by introduction of a liquid distension media at a pressure of about 70 mm Hg.

6. A method of preventing intravasation during an intrauterine procedure as in claim 1, further comprising the step of dilating the cervix prior to the transcervically accessing step.

7. A method of preventing intravasation during an intrauterine procedure as in claim 1, wherein the performing a procedure step comprises treating a uterine fibroid.

8. A method of preventing intravasation during an intrauterine procedure as in claim 1, wherein the step of distending the uterus comprises inflating the inflatable device.

9. A method of preventing intravasation during an intrauterine procedure as in claim 1, wherein the performing a procedure step comprises performing a diagnostic procedure.

10. A method of preventing intravasation during an intrauterine procedure, comprising the steps of:
    transcervically accessing the uterus with an elongate tubular sheath;
    introducing a mechanical distension device through the sheath and into the uterus, while the mechanical distension device is in a retracted state;
    distending the uterus by expanding the mechanical distension device from the retracted state into an expanded state so as to distend the uterus and expose a site;
    introducing a surgical device while the mechanical distension device remains within the uterus in the expanded state; and
    performing a surgical procedure at the site with the surgical device and with the mechanical distension device in the expanded state within the uterus,
    wherein the mechanical distension device comprises an expandable basket, wherein the step of introducing the mechanical distension device into the uterus while the mechanical distension device is in a refracted state comprises introducing the expandable basket into the uterus with the expandable basket in a collapsed state.

11. A method of preventing intravasation during an intrauterine procedure as in claim 10, wherein the step of distending the uterus comprises deploying the expandable basket.

12. A method of preventing intravasation during an intrauterine procedure as in claim 10, wherein the transcervically accessing step is accomplished under local anesthesia.

13. A method of preventing intravasation during an intrauterine procedure as in claim 10, wherein the distending step achieves an equivalent distension to that achieved by introduction of a liquid distension media at a pressure of at least 40 mm Hg.

14. A method of preventing intravasation during an intrauterine procedure as in claim 10, further comprising the step of dilating the cervix prior to the transcervically accessing step.

15. A method of preventing intravasation during an intrauterine procedure as in claim 10, wherein the performing a procedure step comprises treating a uterine fibroid.

16. A method of preventing intravasation during an intrauterine procedure as in claim 10, wherein the performing a procedure step comprises performing a diagnostic procedure.

17. A method of performing a procedure in the uterus, comprising the steps of:
- transcervically accessing the uterus with an elongate flexible tubular sheath, having a proximal end, a distal end and at least one lumen extending therethrough, the sheath having an outside diameter of no more than about 9 mm;
- introducing a mechanical distension device through the sheath and into the uterus with the mechanical distension device in a retracted state;
- distending the uterus by expanding the mechanical distension device from the retracted state into an expanded state, and thereby exposing a site;
- introducing a visualization device through the sheath, to visualize the site, while the distension device remains in the uterus in the expanded state;
- introducing a surgical device through the sheath and into the uterus while the distension device remains in the uterus and in the expanded state; and
- performing a surgical procedure at the site with the surgical device and with the mechanical distension device in the expanded state within the uterus, wherein the mechanical distension device comprises an expandable basket, wherein the step of introducing the mechanical distension device into the uterus while the mechanical distension device is in a refracted state comprises introducing the expandable basket into the uterus with the expandable basket in a collapsed state.

18. A method of preventing intravasation during an intrauterine procedure as in claim 17, wherein the step of distending the uterus comprises deploying the expandable basket.

19. A method of performing a procedure in the uterus as in claim 17, wherein the method is a diagnostic method.

20. A method of performing a procedure in the uterus as in claim 17, wherein the method is a treatment for a uterine fibroid.

* * * * *

UNITED STATES PATENT AND TRADEMARK OFFICE
CERTIFICATE OF CORRECTION

PATENT NO. : 7,763,033 B2
APPLICATION NO. : 11/852116
DATED : July 27, 2010
INVENTOR(S) : Gruber et al.

It is certified that error appears in the above-identified patent and that said Letters Patent is hereby corrected as shown below:

On the Title Page Item 54 (Title), Please change "SYSTEM" to --SYSTEMS;--.

In Column 1, Line 1 (Title), Please change "SYSTEM" to --SYSTEMS;--.

In Column 3, Line 34, Please Change "8A." to --8A;--.

In Column 3, Line 44, Please Change "9A." to --9A;--.

In Column 8, Line 4, Please Change "electromagnetic" to --electro-magnetic--.

In Column 12, Line 19, After "introducers" insert --.--.

In Column 31, Line 61, In Claim 1, change "refracted state" to --retracted state--.

In Column 32, Line 45, In Claim 10, change "refracted state" to --retracted state--.

In Column 34, Line 7, In Claim 17, change "refracted state" to --retracted state--.

Signed and Sealed this
Twenty-eighth Day of December, 2010

David J. Kappos
*Director of the United States Patent and Trademark Office*